(12) United States Patent
Coplin et al.

(10) Patent No.: US 7,867,196 B1
(45) Date of Patent: *Jan. 11, 2011

(54) PUMP AND METHOD HAVING REDUCED PRESSURE AND FRICTION FOR PROVIDING FLUID, ESPECIALLY FOR SURGICAL PROCEDURES

(75) Inventors: Allan Coplin, Fort Lauderdale, FL (US); Joseph J. Cerola, Delray Beach, FL (US)

(73) Assignee: Medsafe, LLC, Fort Lauderdale, FL (US)

( * ) Notice: Subject to any disclaimer, the term of this patent is extended or adjusted under 35 U.S.C. 154(b) by 1327 days.

This patent is subject to a terminal disclaimer.

(21) Appl. No.: 11/225,776

(22) Filed: Sep. 13, 2005

(51) Int. Cl.
 *A61M 37/00* (2006.01)
(52) U.S. Cl. ..................................... 604/131
(58) Field of Classification Search ................ 604/500, 604/28, 30, 35, 151; 417/377, 405; 415/141, 415/904; 418/259, 266
See application file for complete search history.

(56) References Cited

U.S. PATENT DOCUMENTS

| | | | |
|---|---|---|---|
| 3,575,530 A * | 4/1971 | Hall | 416/131 |
| 3,635,583 A * | 1/1972 | Chilman et al. | 416/48 |
| 3,636,609 A * | 1/1972 | Stahl | 269/37 |
| 4,236,589 A | 12/1980 | Griffith | |
| 4,604,089 A | 8/1986 | Santangelo et al. | |
| 5,019,136 A * | 5/1991 | Elonen et al. | 95/261 |
| 5,484,402 A | 1/1996 | Saravia et al. | |
| 5,542,918 A | 8/1996 | Atkinson | |
| 5,718,668 A | 2/1998 | Arnett et al. | |
| 5,807,313 A | 9/1998 | Delk et al. | |
| 6,958,058 B1 * | 10/2005 | Hunter et al. | 604/500 |

OTHER PUBLICATIONS

U.S. Appl. No. 10/454,920, filed Jun. 2003, Hunter et al.

* cited by examiner

*Primary Examiner*—Manuel A Mendez
(74) *Attorney, Agent, or Firm*—Laurence A. Greenberg; Werner H. Stemer; Ralph E. Locher

(57) ABSTRACT

A pump includes a pumping chamber having an inlet, an assembly of a rotating hub and blades disposed in the pumping chamber, a connection to a fluid source and a connection to an air source. According to one embodiment, at least one conduit relieves pressure on the assembly by conducting fluid. According to another embodiment, the blades each have a radially outer edge with a shape minimizing friction between the radially outer edge and an inner surface of the pumping chamber. Methods for providing fluid are also provided.

48 Claims, 31 Drawing Sheets

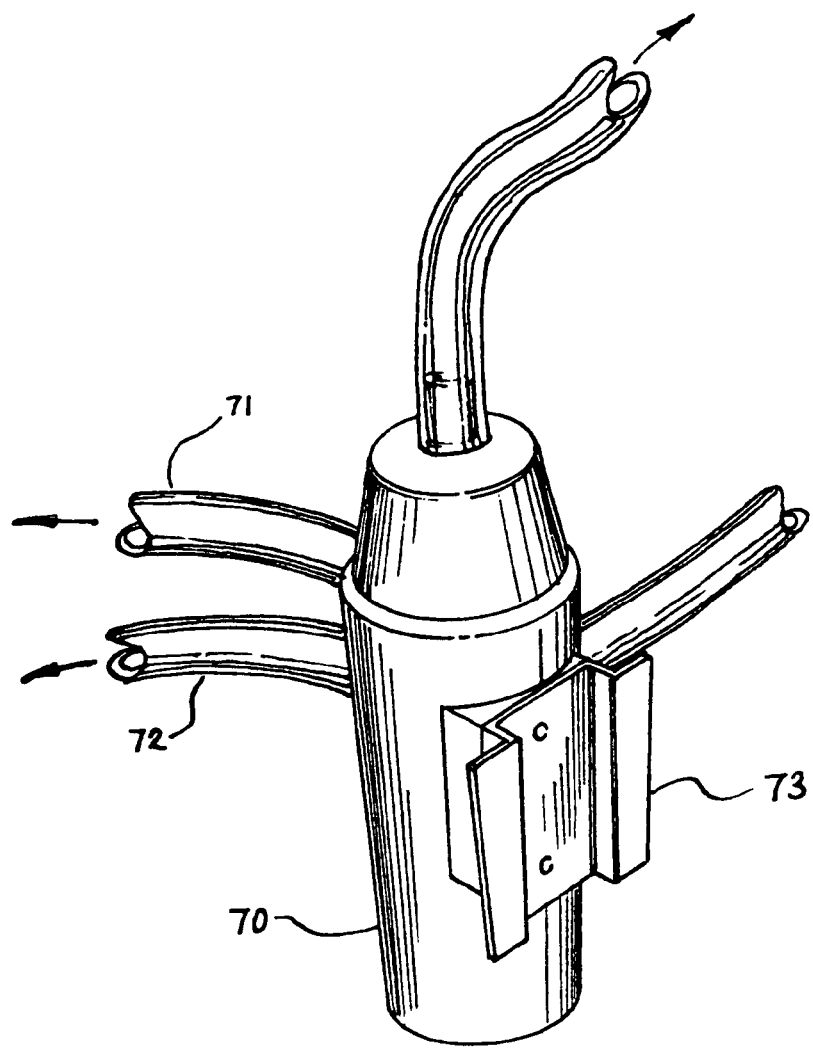
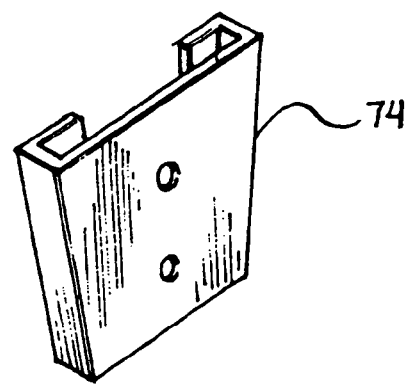
FIG. 7

FIG. 14A
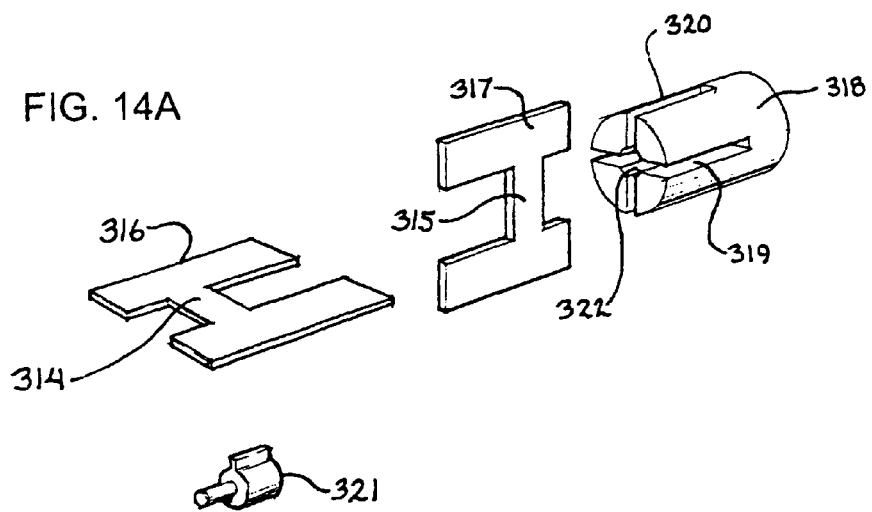
FIG. 14D
FIG. 14B
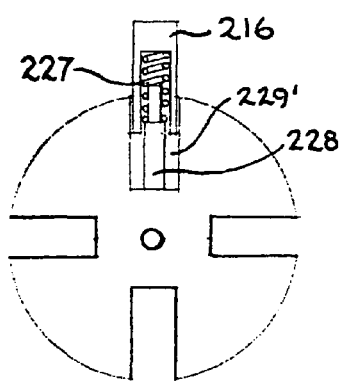
FIG. 14C
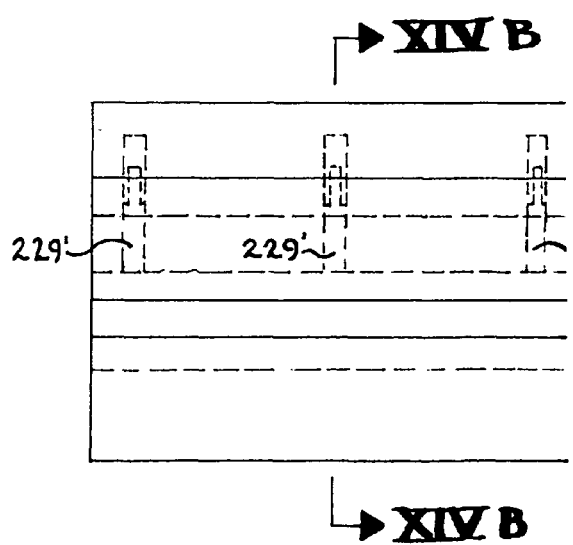

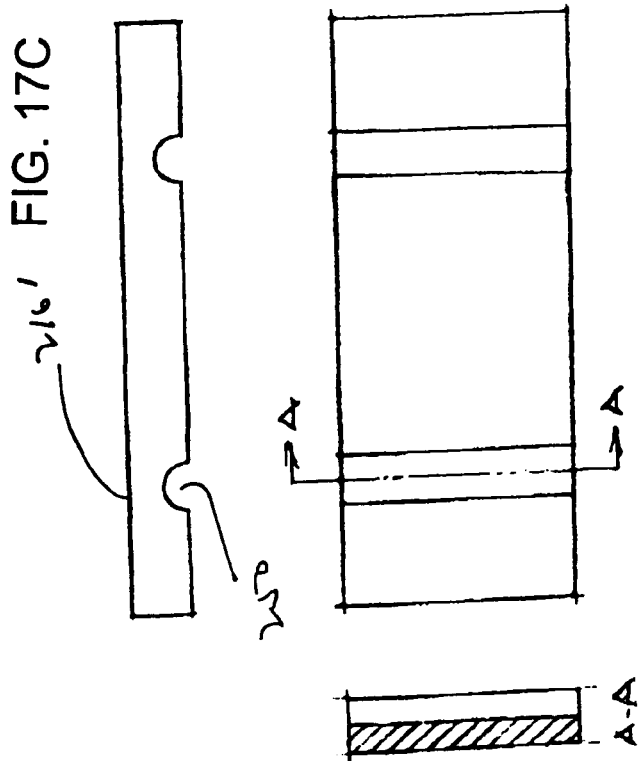
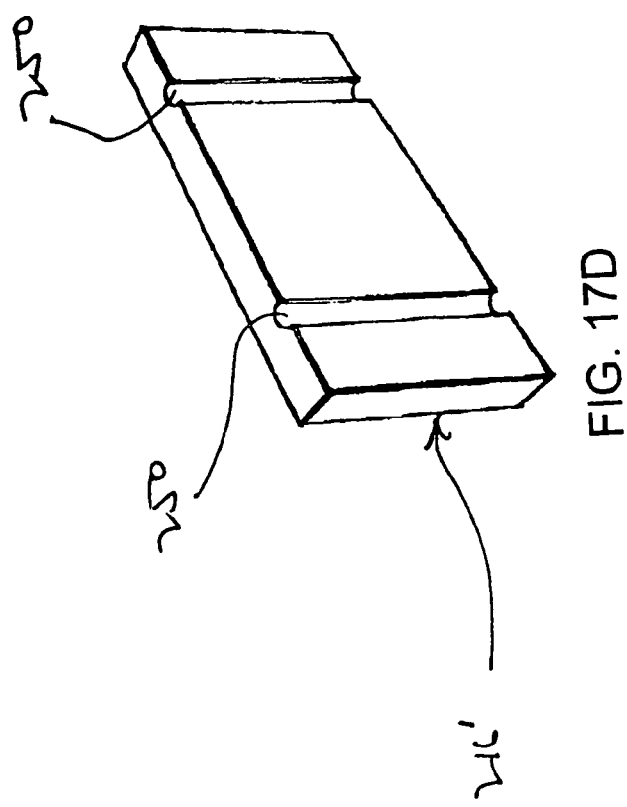

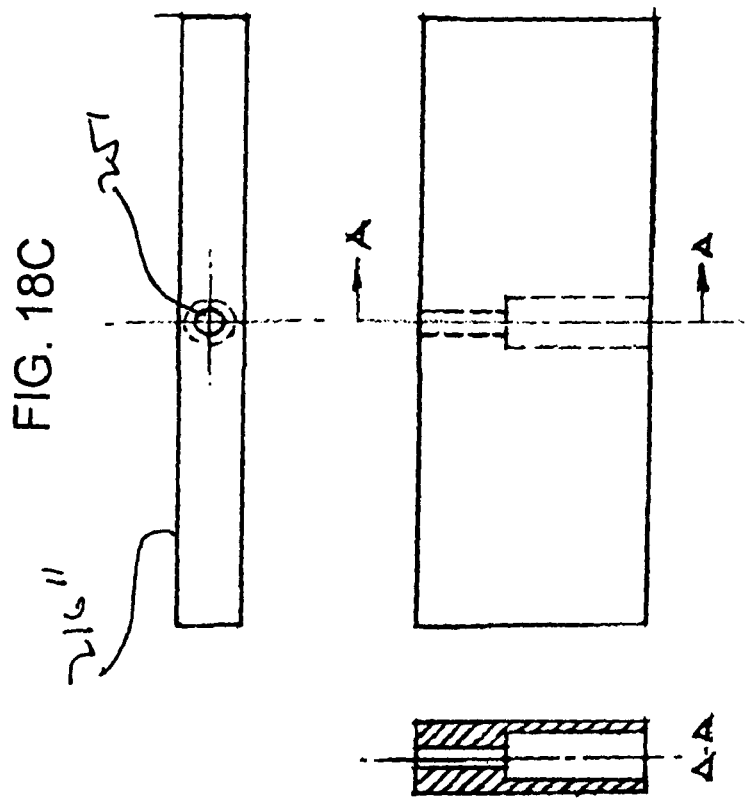
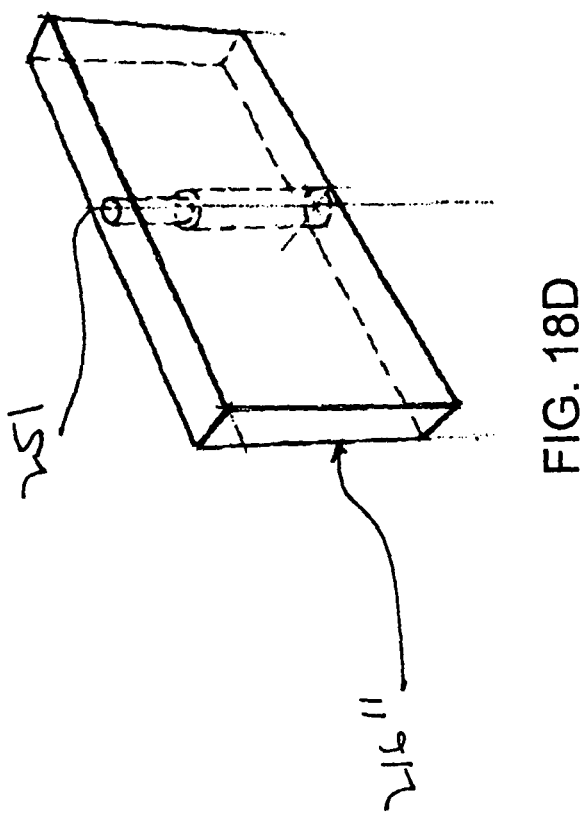

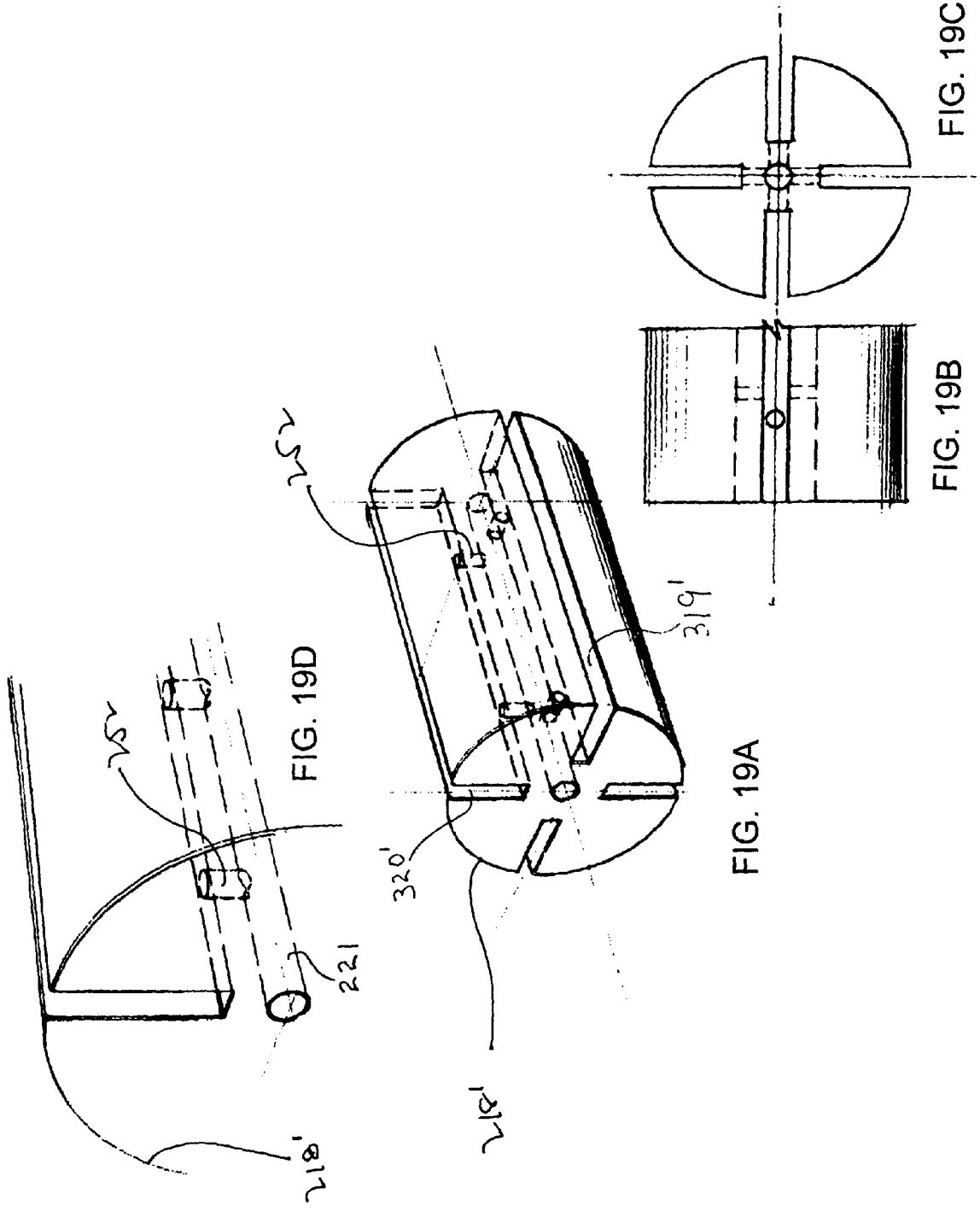

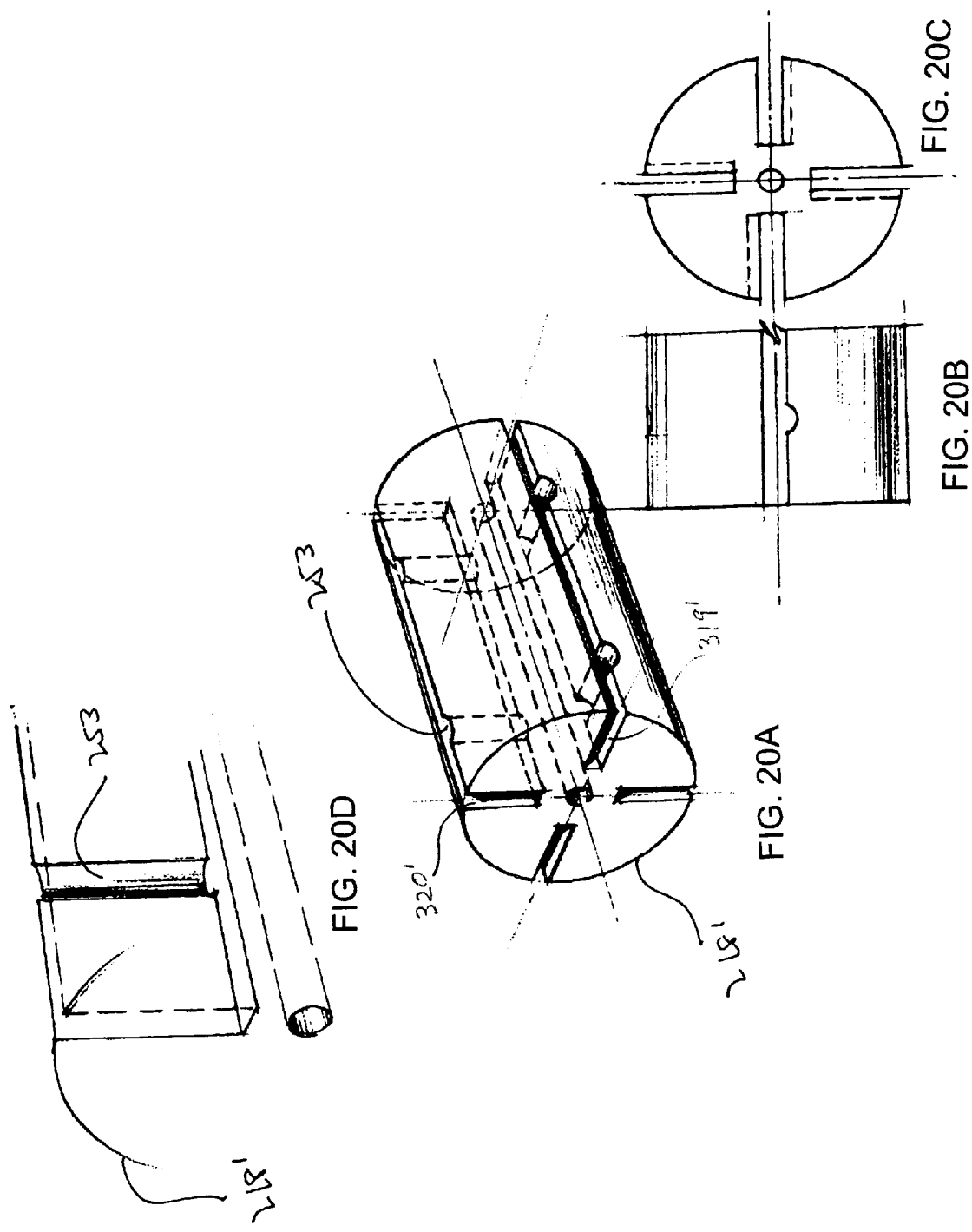

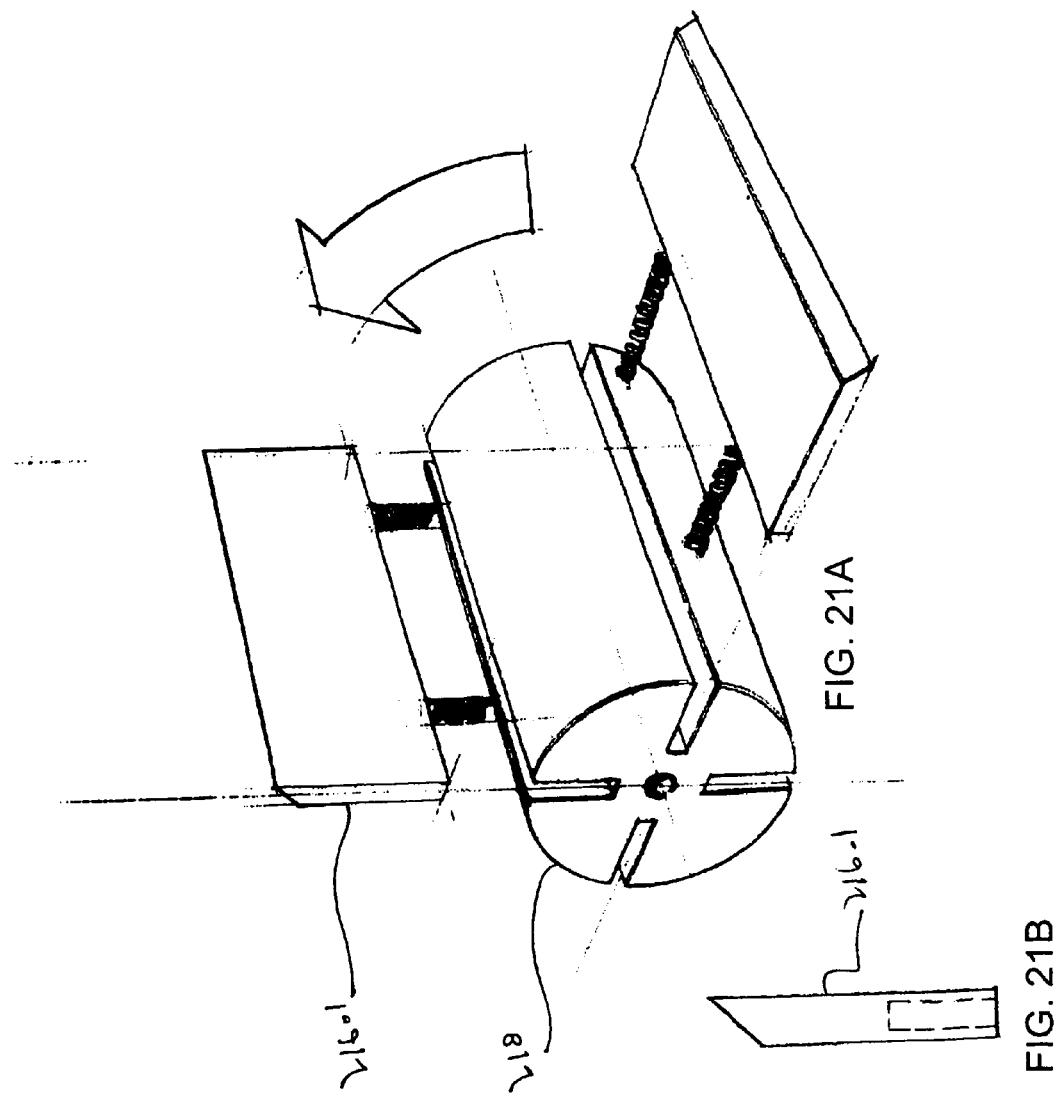

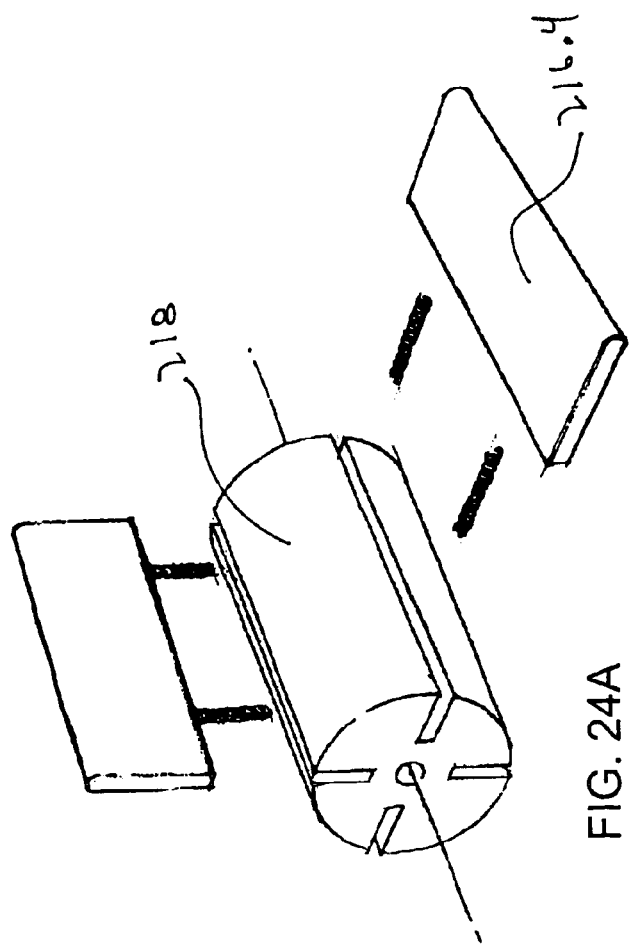
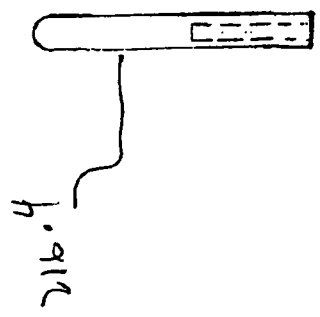
FIG. 24A
FIG. 24B

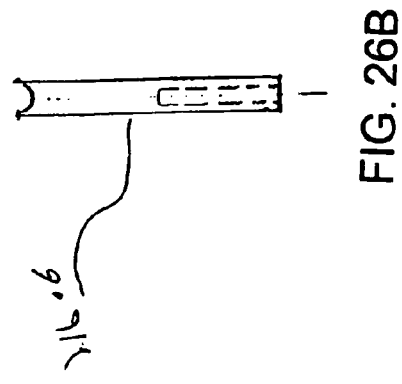
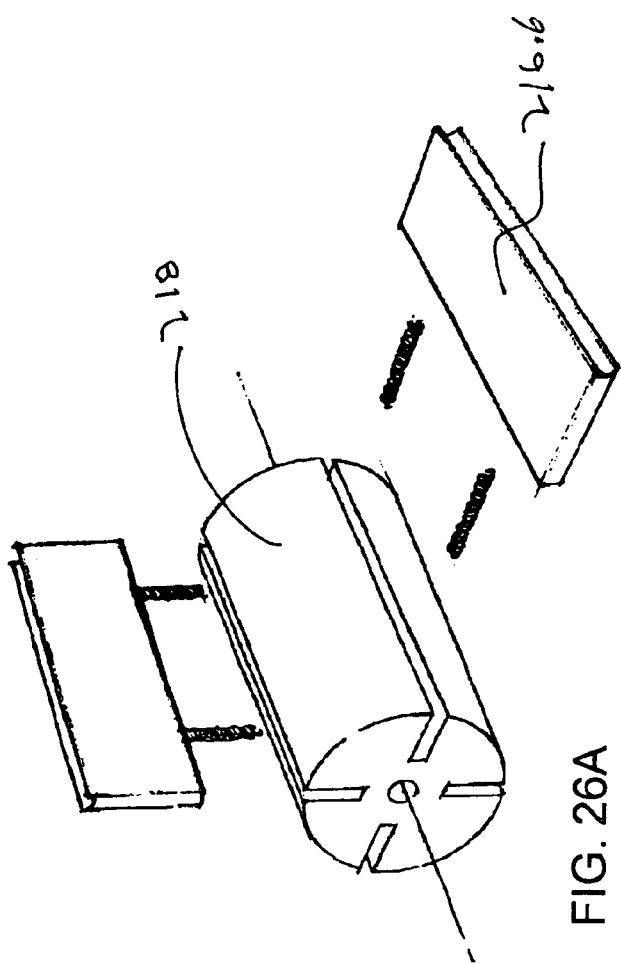

PUMP AND METHOD HAVING REDUCED PRESSURE AND FRICTION FOR PROVIDING FLUID, ESPECIALLY FOR SURGICAL PROCEDURES

BACKGROUND OF THE INVENTION

Field of the Invention

The present invention relates to pumps and methods having reduced pressure and friction for providing fluid, especially for surgical procedures. More particularly, the present invention relates to methods and devices for endoscopic surgical procedures requiring irrigation and suction.

Devices and methods of providing irrigation fluid and suction to a surgical site to irrigate and evacuate the tissue in the area of the surgical procedure are well known in the art. Such devices generally provide a handle member having a switching device for turning on and off the flow of the fluid provided and also for turning on and off the suction provided. Typically, both the suction source and the fluid source are individually connected through an elongated flexible tubular member to a pump or suction source which are positioned adjacent to the surgical site. Typically, the devices communicate with an external pump source to provide the fluid under pressure to the surgical site.

Minimally invasive surgery (MIS) is the art of performing surgical procedures through several small holes in the body, as opposed to open surgery, which involves an incision to expose the entire surgical field. During an MIS procedure, a sterile irrigation solution is used to wash the area to keep the operative field clean and visible. The irrigant is typically provided in sterile plastic disposable bottles or plastic intravenous bags. The suction force is provided by a vacuum that is available through a connection in the operating room wall or is provided by other measures such as a portable suction machine used in small ambulatory surgical sites.

The device used to control the irrigation and suction is called a suction/irrigation tubing set. Generally, this set consists of two lengths of tubing, one to transport the irrigant and the other for suction. The tubes are attached to a small plastic valve that usually controls the irrigation and suction with two buttons that are similar to the valves on a trumpet. Such a valving mechanism is referred to as a trumpet valve. Such trumpet valves are part of tubing kits available from Allegiance Healthcare, Part Number ASC1200, and from Davol, Inc., Part Number 5202730. Another orifice of the device is connected to a probe which is inserted into the body and performs various activities during the surgical procedures.

Irrigating solutions are pumped into the surgical field by a variety of measures. Those measures include pressurized sterile solution bottles, intravenous bags attached to squeezing mechanisms that force the fluid from the bag, and small disposable battery powered pumps that are packaged with each suction/irrigation tubing set. In addition, there are "hybrid" units which are formed of a power unit, that is connected to wall electricity in the operating room and which provides the power for the pumping unit, that is attached to the trumpet valve tubing set and is disposable.

Early irrigating devices included using solution bags that were hung above the surgical area to provide a head pressure that could be used to gently wash the surgical field. Generally, the irrigating fluid needs to be provided with more force than that supplied by simple head pressure on a fluid, and thus, irrigating fluids are provided using pumps. U.S. Pat. No. 5,484,402 to Saravia et al. teaches a self-contained pumping unit that is located adjacent to a source of irrigation and is remote from the valving handpiece device. The pumping unit includes a housing containing an outlet for liquid, a pumping member for pumping irrigation liquid through the outlet, a motor for driving the pumping member and an electric battery assembly for energizing the motor. An elongated tube connects the pumping outlet to the handpiece irrigation liquid inlet for supplying pumped irrigation liquid to the handpiece.

Another battery powered device is disclosed in U.S. Pat. No. 5,807,313 to Delk et al. A battery powered laproscopic and endoscopic irrigator is taught therein. The pumping unit includes an upper portion that connects directly to an irrigation reservoir holding an irrigation solution such as saline. A lower portion of the pump connects to the batteries. The upper portion of the pump includes a pump, a motor and attachments connecting the upper and lower portions. During the manufacturing of the pump, batteries are inserted into the lower portion and the upper portion is connected to the lower portion via clips. The pump is constructed to hang vertically from the irrigation source and to direct the irrigation fluid source downwardly with some force. There is a wire extending through the bottom of the pumping unit connecting the upper portion with the batteries and motor.

A pulsating battery pump is taught in U.S. Pat. No. 5,718,668 to Arnett et al. The handpiece contains a mechanism used to supply irrigant in a pulsating manner to the surgical site. The pump provides a reciprocally driven device for pumping pulses of irrigation liquid through an outlet device, and a powered drive device for reciprocally driving the pump.

Those battery powered pumps require the presence of switch and a wire that runs from the pump to the trumpet valve. Some battery powered pumps require a pressure switch or a manually operated switch and a wire connection between the switch and the pump. Those additional features, such as the switch and wire connection, add to the complexity of the battery powered pump and provide for sites for mechanical failure and difficulty in manufacture. Additionally, operating such a pump may add extra considerations for the surgeon during an operation.

The prior art also provides a vacuum-driven pumping device. In U.S. Pat. No. 5,542,918 to Atkinson, a fluid pump using a trumpet valve and a vacuum-driven pump is described. The pump is operated using a piston arrangement that includes springs. However, one of the disadvantages of this device is the number of parts used makes the device costly. Additionally, the device uses a pistol grip configuration rather than the more acceptable trumpet valve configuration. Also, the device must have pressure controls or it generates too much pressure for the procedures and could be dangerous.

U.S. Pat. No. 4,236,589 to Griffith discloses a vacuum motor, but has no pump which is the subject of the invention of the instant application.

U.S. Pat. No. 4,604,089 to Santangelo et al. discloses a medical irrigation system having a pump. It is stated therein that the pump may be a vacuum pump, but no details of such a pump are given.

Accordingly, what is needed are devices for surgical procedures, such as endoscopic and laparoscopic procedures, that are simple, yet provide both suction and irrigation with pressure provided by a pump that does not need an additional power source. What is also needed are methods of use of such devices to improve surgical procedures.

Allowed U.S. application Ser. No. 10/454,920, filed Jun. 10, 2003, which issued as U.S. Pat. No. 6,958,058 on Oct. 25, 2005, provides a pump and a method for providing fluid which fulfils the need for such pumps and methods while overcoming the shortcomings of the prior art. However, trapped fluid under the blades in the hub produces pressure keeping the blades from moving in the slots and pressure is also present between the blades. The pressure limits the speed of rotation of the rotor and therefore the efficiency and output of the pump.

In addition, friction between the outer edges of the blades and the inner surface of the pump chamber also limits the speed of rotation of the rotor and therefore the efficiency and output of the pump.

SUMMARY OF THE INVENTION

It is accordingly an object of the invention to provide pumps and methods having reduced pressure and friction for providing fluid, especially for surgical procedures, such as endoscopic and laparoscopic procedures, which overcome the hereinafore-mentioned disadvantages of the heretofore-known methods and devices of this general type and in which pressure caused by trapped fluid under the blades in the hub and pressure between the blades is relieved, and friction between the outer edges of the blades and the inner surface of the pump chamber is minimized.

With the foregoing and other objects in view, there is provided, in accordance with the invention, a pump, comprising a pumping chamber having an inlet, and an assembly disposed in said pumping chamber. The assembly has a rotating hub, blades mounted on said rotating hub, and at least one conduit relieving pressure on said assembly by conducting fluid. A connection to a fluid source and a connection to an air source are provided.

In accordance with another feature of the invention, the at least one conduit is at least one radially directed channel formed in at least one outer surface of the blades for relieving said pressure on said assembly by conducting trapped fluid radially outwardly. The at least one conduit may also be at least one radially directed hole formed in each of said blades for relieving said pressure on said assembly by conducting trapped fluid radially outwardly. The at least one conduit may additionally be at least one hole passing through said blade from one lateral surface to another for relieving said pressure on said assembly by conducting fluid through said at least one hole.

In accordance with a further feature of the invention, the at least one conduit is at least one radially directed hole formed in each bottom of each slot receiving said blades, for relieving said pressure on said assembly by conducting trapped fluid from said slot bottoms, for example into a hole in the hub for a rotor shaft. The at least one conduit may also be at least one radially directed channel formed in at least one lateral surface of the slots for relieving said pressure on said assembly by conducting trapped fluid radially outwardly.

In accordance with an added feature of the invention, there is provided an air motor chamber having an inlet. Another assembly disposed in said air motor chamber has a rotating hub and blades mounted on said rotating hub. The assemblies rotate together. End caps may each be disposed at a respective one of said chambers. The end cap of said air motor chamber has ports and blind pockets formed therein for conducting air to create different pressures at surfaces of said blades in said air motor chamber for rotating said blades.

In accordance with an additional feature of the invention, the pump pumps the fluid for a procedure selected from the group consisting of laparoscopy, open surgery, orthopedics, oral surgery, arthroscopy, endoscopy, wound cleansing, liposuction and gynecology.

With the objects of the invention in view, there is also provided a pump, comprising a pumping chamber having an inner surface and an inlet, and an assembly disposed in said pumping chamber. The assembly has a rotating hub and blades mounted on said rotating hub. The blades each have a radially outer edge with a shape minimizing friction between said radially outer edge and said inner surface of said pumping chamber. A connection to a fluid source and a connection to an air source are provided.

In accordance with another feature of the invention, the hub rotates in a direction of rotation, and said radially outer edge is beveled along or against said direction of rotation. The radially outer edge may also have two intersecting bevels. The radially outer edge may additionally be rounded. The radially outer edge may have a surface perpendicular to said lateral surfaces of the blades. Finally, the radially outer edge may be concave.

With the objects of the invention in view, there is additionally provided a method for providing fluid, which comprises providing a pump connected to a source for fluid and a source for air. The pump has an assembly with a rotating hub and blades mounted on the rotating hub. The pump is driven with a vacuum. The fluid is pumped to a site. Pressure on the assembly is relieved by conducting fluid through at least one conduit.

In accordance with another mode of the invention, the step of relieving pressure on the assembly is carried out by conducting trapped fluid radially outwardly through at least one respective radially directed channel formed in at least one outer surface of each of the blades.

In accordance with a further mode of the invention, the step of relieving pressure on the assembly is carried out by conducting trapped fluid radially outwardly through at least one respective radially directed hole formed in each of the blades.

In accordance with an added mode of the invention, the step of relieving pressure on the assembly is carried out by conducting fluid through at least one hole passing through each respective one of the blades from one lateral surface to another lateral surface of the blades.

In accordance with an additional mode of the invention, blade-receiving slots with slot bottoms are provided in the hub, and the step of relieving pressure on the assembly is carried out by conducting trapped fluid through at least one respective radially directed hole formed in each slot bottom.

In accordance with yet another mode of the invention, blade-receiving slots with lateral surfaces are provided in the hub, and the step of relieving pressure on the assembly is carried out by conducting trapped fluid through at least one radially directed channel formed in at least one of the lateral surfaces.

With the objects of the invention in view, there is furthermore provided a method for providing fluid, which comprises providing a pump connected to a source for fluid and a source for air. The pump has a pumping chamber and an assembly with a rotating hub and blades mounted on the rotating hub. The pump is driven with a vacuum. The fluid is pumped to a site. Friction between radially outer edges of the blades and an inner surface of the pumping chamber is minimized.

In accordance with another mode of the invention, the hub is rotated in a direction of rotation, and the step of minimizing friction between radially outer edges of the blades and an inner surface of the pumping chamber is carried out by beveling the radially outer edges along or against the direction of rotation.

In accordance with a further mode of the invention, the step of minimizing friction between radially outer edges of the blades and an inner surface of the pumping chamber is carried out by providing each of the radially outer edges with two intersecting bevels.

In accordance with an added mode of the invention, the step of minimizing friction between radially outer edges of the blades and an inner surface of the pumping chamber is carried out by rounding each of the radially outer edges.

In accordance with an additional mode of the invention, the step of minimizing friction between radially outer edges of the blades and an inner surface of the pumping chamber is carried out by providing the blades with lateral surfaces and providing each of the radially outer edges with a surface perpendicular to the lateral surfaces.

In accordance with a concomitant mode of the invention, the step of minimizing friction between radially outer edges of the blades and an inner surface of the pumping chamber is carried out by providing the radially outer edges with a concave shape.

Other features which are considered as characteristic for the invention are set forth in the appended claims.

Although the invention is illustrated and described herein as embodied in pumps and methods having reduced pressure and friction for providing fluid, especially for surgical procedures, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 7 is an external, perspective view of an embodiment of the present invention which is capable of being attached to a wall or other structure support device;

FIGS. 14A, 14B, 14C and 14D are respective exploded-perspective, cross-sectional, side-elevational and perspective views illustrating an assembly of valve blades;

FIGS. 17A, 17B, 17C and 17D are respective front-elevational, side-elevational, top-plan and perspective views of liquid pump rotor blades having pressure relief channels;

FIGS. 18A, 18B, 18C and 18D are respective front-elevational, side-elevational, top-plan and perspective views of liquid pump rotor blades having pressure relief holes;

FIGS. 19A, 19B, 19C and 19D are respective perspective, side-elevational, end-elevational and enlarged, fragmentary perspective views of a liquid pump rotor having pressure relief holes in bottoms of blade slots;

FIGS. 20A, 20B, 20C and 20D are respective perspective, side-elevational, end-elevational and enlarged, fragmentary perspective views of a liquid pump rotor having pressure relief channels;

FIGS. 21A and 21B are respective exploded perspective and side-elevational views of a rotor and blades having an edge beveled along the direction of rotation of the blade;

FIGS. 24A and 24B are respective exploded perspective and side-elevational views of a rotor and blades having a convexly rounded edge;

FIGS. 26A and 26B are respective exploded perspective and side-elevational views of a rotor and blades having a concave edge;

DESCRIPTION OF THE PREFERRED EMBODIMENTS

Figure 1:
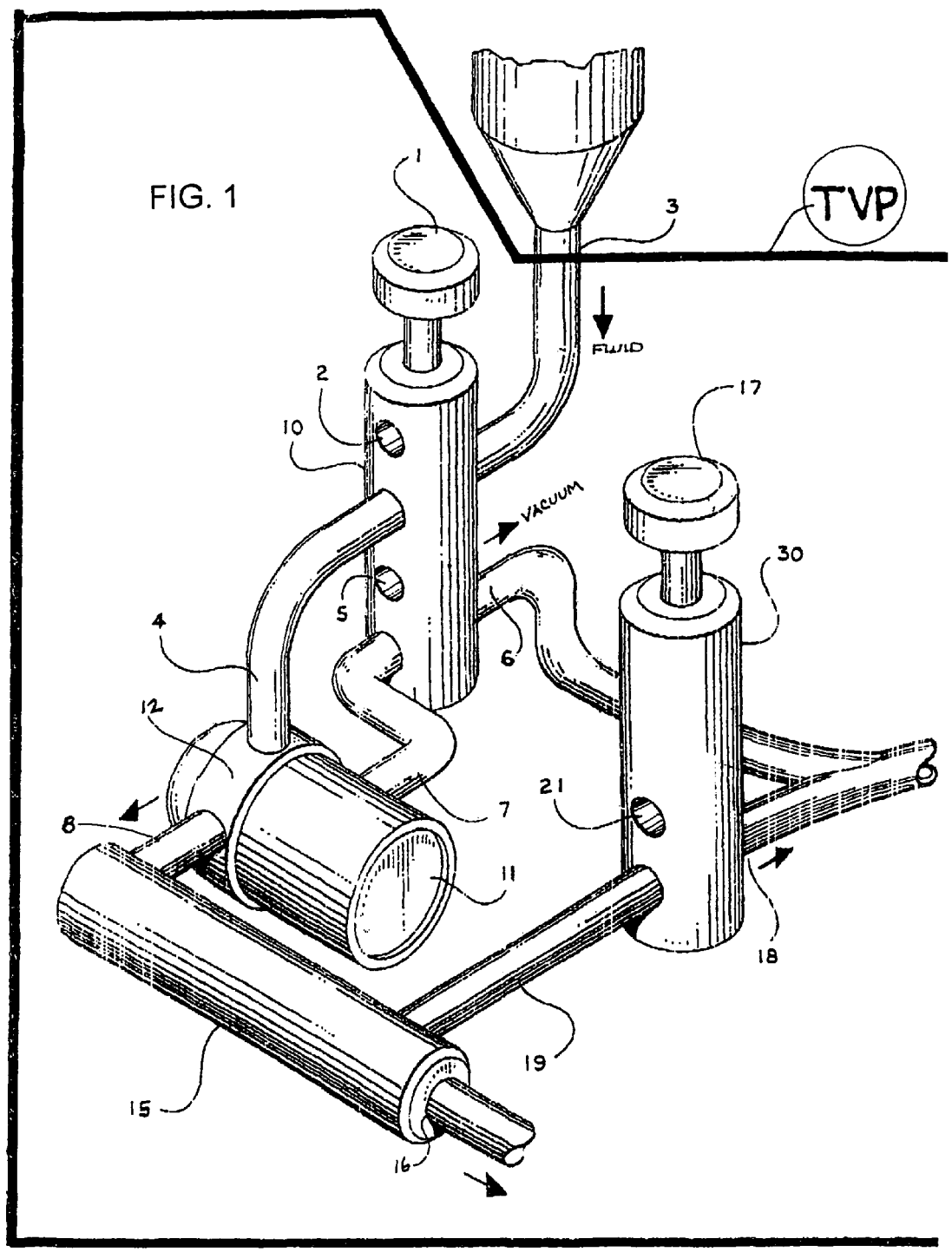
FIG. 1 is a fragmentary, diagrammatic, perspective view of the trumpet valve and pump combination of the present invention in which valves are closed.

The present invention includes devices and methods of use of such devices in surgical procedures. Surgical devices that provide irrigating fluid and suction to a surgical field are known in the art. Those devices are important to a clinician in irrigating a surgical site and evacuating debris from the site.

Devices currently used in the art typically provide a handle member having a device for turning on or off the flow of the irrigating fluid, together with a device for controlling the suction. Some devices provide for simultaneous suction and irrigation. Generally, the suction source and the fluid source are connected to the device by a flexible tubing configuration and they are positioned adjacent the surgical site. Those devices provide the irrigating fluid under pressure by use of an external pumping device or provide fluid with only minimal head pressure.

The present invention includes devices that are capable of providing irrigating fluid under pressure. The present invention provides a trumpet valve and pump combination having a stand-alone pump that is vacuum-driven using a hub and movable blade system to provide irrigation for surgical procedures. Alternative embodiments of the present invention include vacuum-driven pumps that are integrated with the irrigating and suction functions of the devices.

Preferred embodiments of the present invention include vacuum-driven pumps that are separate, or external, from the irrigation fluid delivery portion of the device, such as the valve or probe portions. The irrigation/suction devices in the art, prior to the present invention, use additional sources of energy to provide the irrigating fluid under pressure or use sources that are unreliable. The energy used is either air pressure, batteries, or electricity provided in the operating theatre. External pumps may be located in areas separate from the valve device, and are disposed adjacent the surgical field by attachment to an intravenous solution bag, hanging on a support pole, or an adjacent table or stand, freestanding on the floor or attached to a wall or in the cover of a suction canister used in the operating room.

The present invention includes devices having a pumping device that is driven by a vacuum force available in the operating theatre. Such suction force may be provided by the operating theatre, either by an in-house vacuum system provided through an outlet in the room, or by suction created by any measures. Preferably, the present invention includes a stand-alone vacuum-driven pump, external to a valve device or irrigation and suction control device. Such a preferred embodiment includes methods of placement of the pump that have attachments to intravenous bags, support structures or freestanding pumps capable of being placed on the floor or other sites within the operating theatre. By operating as a stand-alone device, the pump provides greater flexibility in terms of use and/or placement during procedures. Additionally, the pump may be disposable, if desired, thereby reducing capital costs since the valve or probe portions of the system may be reused.

Another embodiment of the present invention includes a trumpet valve in combination with a motor driven by the available suction power. Yet another embodiment includes an air motor, such as a turbine, in combination with a trumpet valve. The air motor is connected by a device such as a shaft to a pump that is used to provide pressurized fluid to the surgical site.

A preferred method of operation of the devices of the present invention is described herein. As discussed, the pump is preferably a stand-alone pump separate from the valve or probe portions of the fluid delivery system. As such, when irrigation is required, a valve piston head, connected to the operative stem of an irrigation valve, is depressed. The air motor then activates the pump, and the pumping action provides the force to drive the irrigating fluid under pressure to the surgical site. In is noted that the pump may or may not be running all the time. The selection as to whether or not the pump runs continuously depends on the relative dimensions of the pump. However, irrigation is delivered to the surgical site when the valve is depressed. The force of the fluid and amount of fluid provided are controlled by the length of depression of the valve piston head. Preferably, the valve piston head is part of a trumpet valve.

According to one mode of operation, when suction of debris is desired, the irrigation valve is released, closing the irrigation device and stopping the pump. The other valve piston head is then depressed, activating the suction function. The debris is then removed from the surgical site and displaced into an attached receptacle that is separate from the devices of the present invention and the surgical field. In a most preferred embodiment, the connections used in the present invention are connections to the irrigation fluid source and to the suction source.

Alternatively, the vacuum-driven pump may be integrated with the device by which the irrigating and suction functions are operated, such as a trumpet valve. In this embodiment, the pump and valve are included as one unit wherein depression of one of the trumpet pistons directly results in the activation of the irrigation or suction functions of the device.

The devices of the present invention may be made of any material, though preferably, the devices are made from plastic and may be easily manufactured. The material may be transparent, translucent or opaque. Most preferably, the devices of the present invention are disposable so that sterility is assured and costs are lower. The present invention contemplates embodiments that can be reused by sterilization following each use of the device. The costs of the present invention are significantly lower than that of devices currently available because there is no need for an external power source. Additionally, when the present invention is used as a stand-alone pump, the pump and the motor may be constructed to be separate so that only the pump and the trumpet valve are disposed of while the motor may be reused, lowering costs as well.

As stated previously, the most preferred embodiments of the present invention utilize devices including the pumps of the present invention wherein the pumps are stand-alone and are separate from the valve device. For example, the air motor and pumping device could be in a separate housing adjacent the valve device. See FIGS. 6 through 10 for embodiments of the present invention wherein the pump is separate from the valve or control device.

Figure 11:
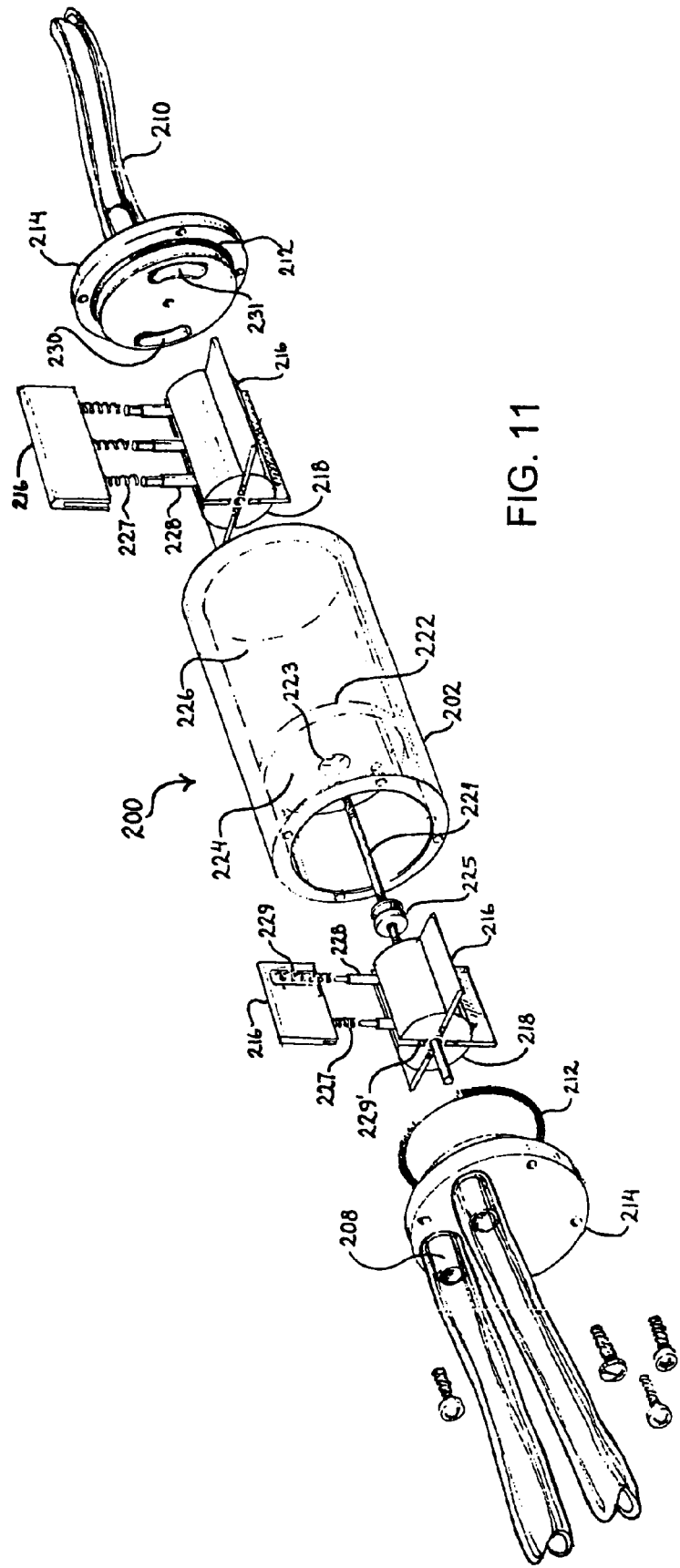
FIG. 11 is an exploded, perspective view of a stand-alone pump according to one embodiment of the present invention.

The vacuum motor driving the pump includes a rotary device having a hub and blades that adjust depending on the location of the blade in relation to the air motor chamber. This is as a result of the hub being offset from the middle of the air motor chamber. Being offset permits the blades to rotate due to air drawn through into the chamber by operation of the vacuum suction action. In a preferred embodiment, the blades are offset from each other on the hub at 90° angles and the blades are not connected but ride on springs. The springs are placed in the hub such that the blades may move in and out. Accordingly, when one blade is pushed toward the hub, such as by the inner wall of the air motor chamber, the corresponding blade on the other side is pushed away from the hub and into the path of the air, thereby causing the blade to be pushed, turning the rotary piston to power the device. One embodiment is shown in FIG. 11, wherein the air motor includes two sets of two blades, wherein one set of blades is perpendicular to the other. However, while four blades are shown, the number of blades may vary, but are preferably even in number.

Alternatively, the present invention includes pumps having vanes and a rotor on the center line of the pumping chamber.

Alternatively, the motor driving the pumping device could be run by sources other than vacuum, such as air pressure, that is any pneumatic source. Other types of air motors that are contemplated by the present invention include, but are not limited to, roots, rotary piston, rotary screw, liquid ring and turbines. Those motors can be constructed to run off a vacuum source to drive the irrigation fluid. The present invention contemplates the use of any construction for the combined suction and irrigation device, including but not limited to structures such as a standard trumpet valve structure, a pistol grip or a wand-type housing. The structures of the present invention can be changed to meet the needs of the surgical procedures, including but not limited to, laparoscopy, open surgery, orthopedics, oral surgery, arthroscopy, endoscopy, wound cleansing, liposuction and gynecology.

The present invention also facilitates the incorporation of additional elements such as electrocautery, laser attachments, ultrasound attachments, provision of light to the surgical field, attachments for viewing the site, photography or videography of the site, computer mapping of the site, provision of pharmaceuticals, chemotherapeutics or other medicinal compositions to the site, and selective dissection or biopsy capabilities at the surgical site.

An embodiment of the present invention is shown in FIGS. 1-5. This embodiment incorporates the pump with the valve in a single system. The valve, motor and pump are combined in an easily held device that can be operated by either left-handed or right-handed clinicians. The valve is a trumpet-style valve configuration with one chamber connected to both the irrigation and suction sources. This chamber controls the pump and provides the irrigation fluid under pressure to the surgical site. The other chamber is constructed to control the suction action of the device. The trumpet valve and pump configuration TVP has a common housing for the pump and the valve.

The present invention also contemplates devices and methods of use wherein the irrigating fluid is delivered in uniform, pulsatile or other methods or combinations of such methods. Provision of irrigating fluid in such various methods may include adaptors for providing the fluid in the desired method.

Figure 2:
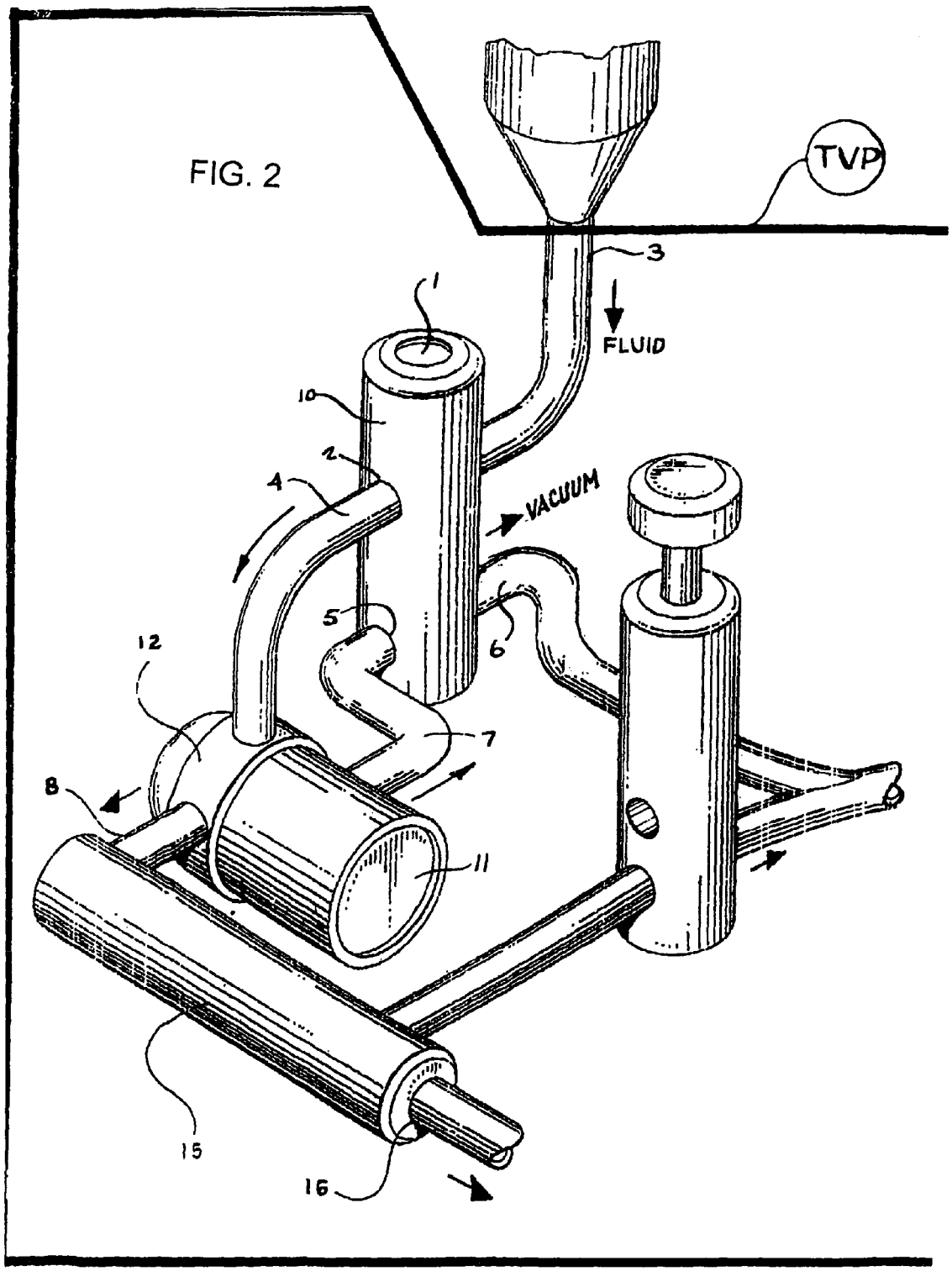
FIG. 2 is a view similar to FIG. 1 in which an irrigation valve is open.

Referring now to the figures of the drawings in detail and first, particularly, to FIG. 1 thereof, there is seen a trumpet valve and pump combination TVP having a valve stem head 1 movably displaced within a valve body 10 and connected to tubes 2 and 5 traversing the interior of valve body 10. The valve stem head 1 is depressible and operates to open a connection to the tube 2 to allow irrigation fluid to flow from the source through tube 3, through tube 2 and into tube 4. When valve stem head 1 is depressed, tube 5 is then connected to tube 6 on one side and tube 7 on the other side. This connection allows suction force to be applied from the vacuum source through tube 6, through tube 5 (through valve body 10) and into vacuum motor 11. This is illustrated in FIG. 2. When valve stem head 1 is depressed, suction force is used to operate vacuum motor 11, which in turn, powers pump 12. Irrigation fluid flowing though tube 4 into pump 12, is pressurized by pump 12 and flows out of pump 12 and into common chamber 15 through tube 8. Common chamber 15 is connected to a probe or other instrument or tubing at fitting 16.

Figure 3:
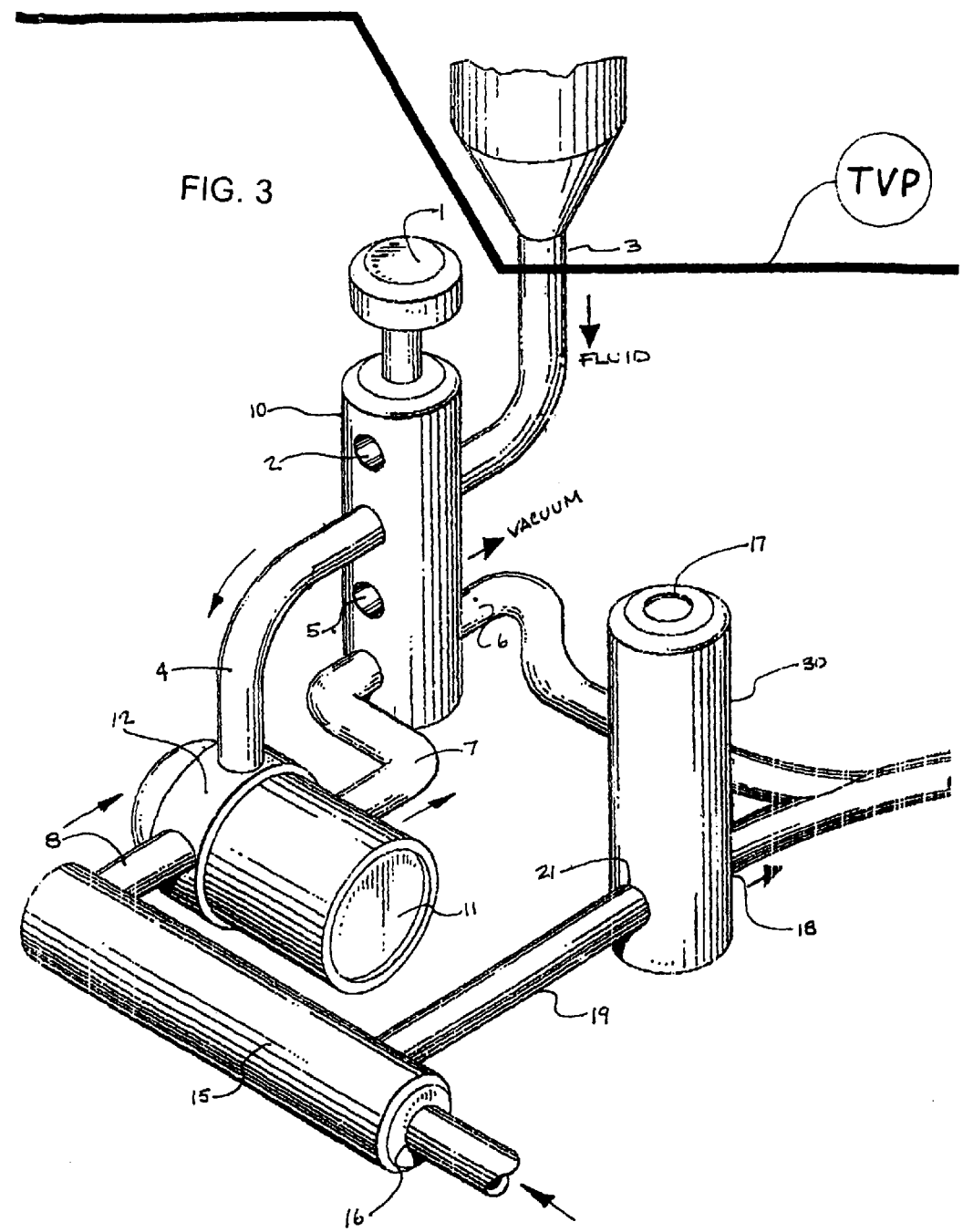
FIG. 3 is another view similar to FIG. 1 in which a suction valve is open.

In FIG. 1, valve stem head 17 is movably displaced within valve body 30 and is connected to tube 21 traversing the valve body 30. Depressing valve stem head 17 opens the connection between tube 18, which is connected to the suction source, and tube 19, which is connected to common chamber 15 by aligning the first opening of tube 21 with the opening of tube 18, and aligning the second opening of tube 21 with the opening of tube 19. Depressing valve stem head 17 creates a suction force in the probe, instrument or tubing attached to fitting 16. This is shown in FIG. 3.

Figure 4:
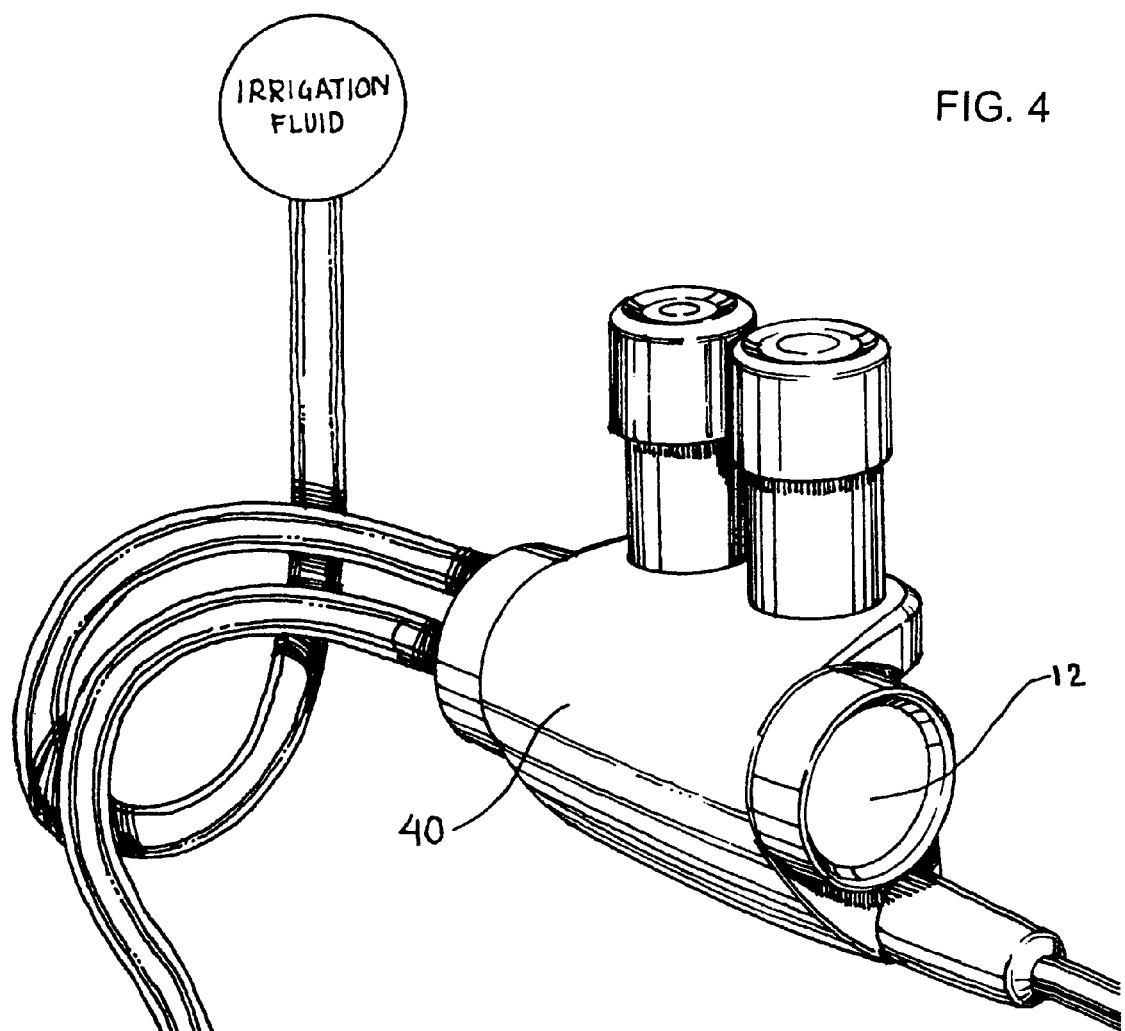
FIG. 4 is an external, perspective view of an embodiment of the trumpet valve and pump combination of the present invention.
Figure 5:
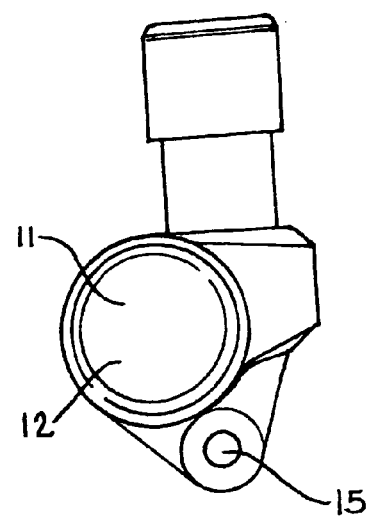
FIG. 5 is an external, side-elevational view of an embodiment of the present invention.

FIG. 4 shows an external view of a preferred embodiment of the present invention having a common housing 40, which may be transparent to permit monitoring of a pumping operation. FIG. 5 shows a fragmentary, side-elevational view of the embodiment of FIG. 4 which illustrates the placement of suction (vacuum) motor 11, pump 12 and common chamber 15.

The present invention relates to suction/irrigation devices for surgical procedures and methods of using such devices. The present invention includes devices that are easy to set-up and that have reduced complexity due to the method of powering since no additional external power source is necessary. The present invention includes lightweight, inexpensive, disposable pumps that are driven by alternative power sources.

Figure 6A:
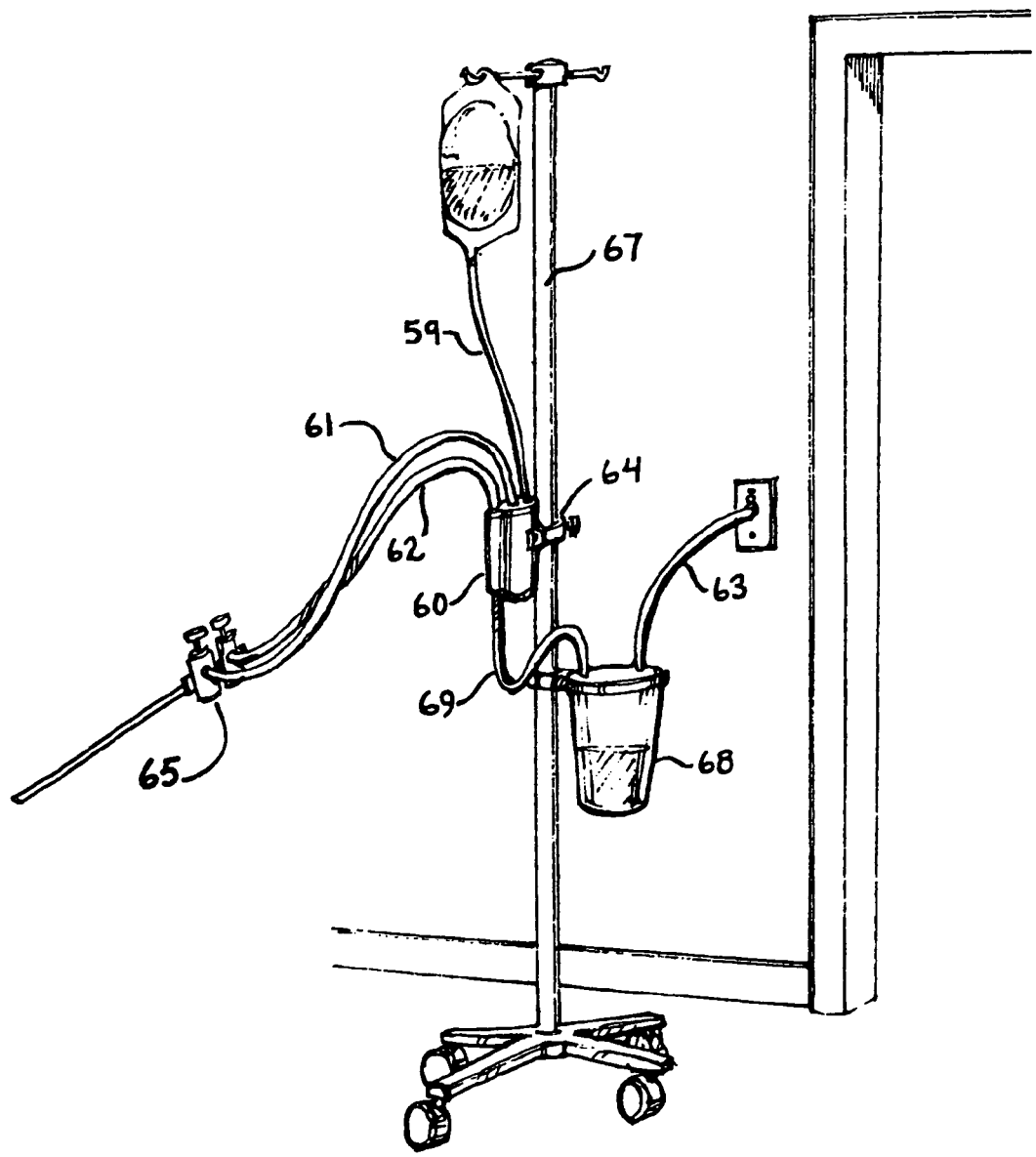
FIG. 6A is a perspective view of an embodiment of the present invention attached to a support pole such as those commonly used in operating theatres.
Figure 6B:
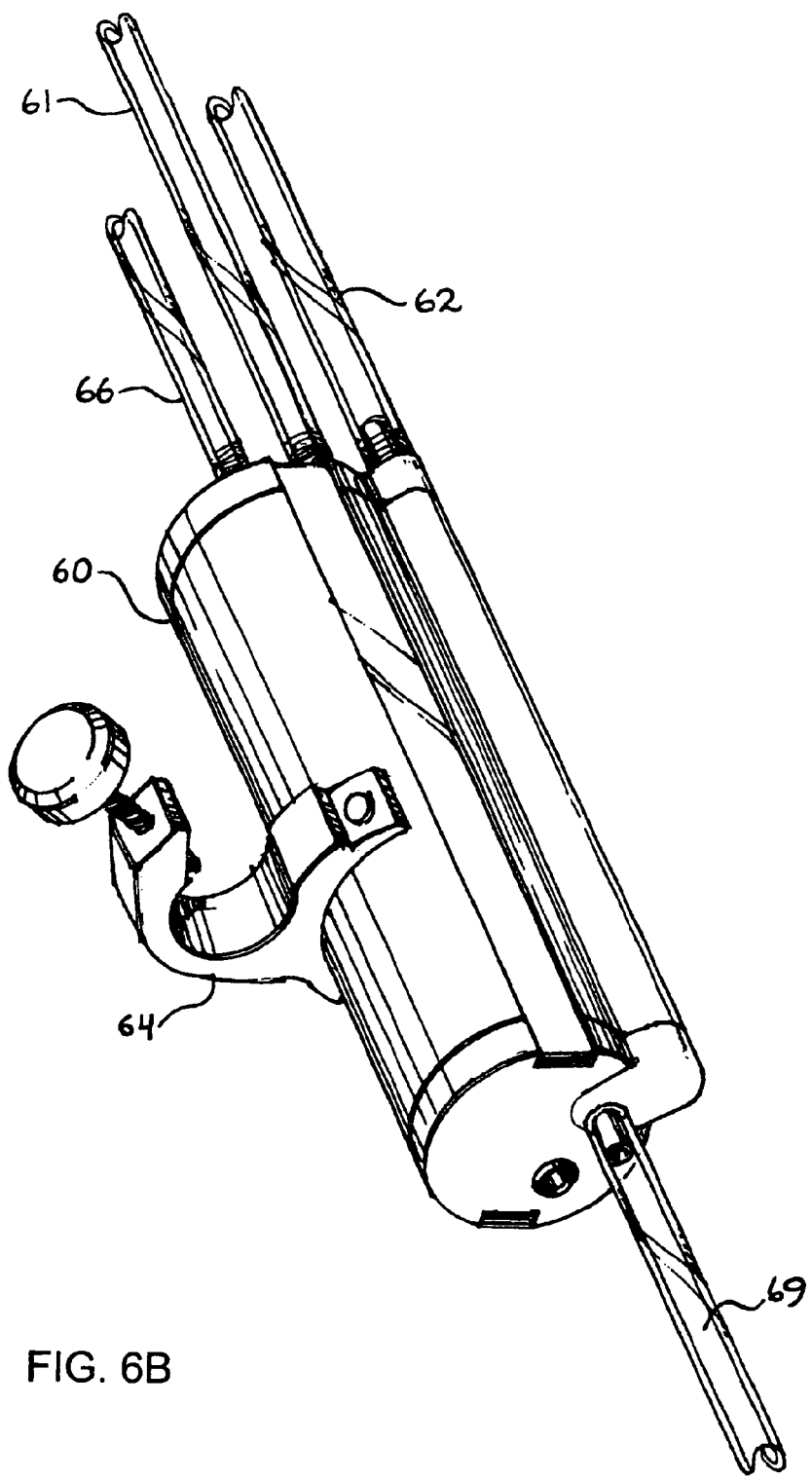
FIG. 6B is an enlarged, perspective view of the pump shown in FIG. 6A.

FIGS. 6A to 10 depict various preferred embodiments of the present invention as used in different procedures and in different manners. FIG. 6A shows a pump 60 which has a trumpet valve irrigation connection 61 and a trumpet valve suction connection 62 and is directly attached to a support pole 67. The support pole 67 is of the type commonly used in operating theatres, using a coupling device 64, such as a spring loaded clamp. Additionally, a suction source 63 and a container 68 may be included. As can be seen, the pump 60 is a stand-alone pump separate from the trumpet valve 65. FIG. 6B is an enlarged, perspective view of the pump 60, showing the clamp 64, the irrigation source connection 61, the suction source connection 62, an IV bag connection 66 and a suction connection 69 leading to the container 68.

FIG. 7 shows a pump 70 having an irrigation source 71 and a suction source 72 and a male 73 and female 74 bracket that permits attachment of the pump to a wall or other structure support device.

Figure 8:
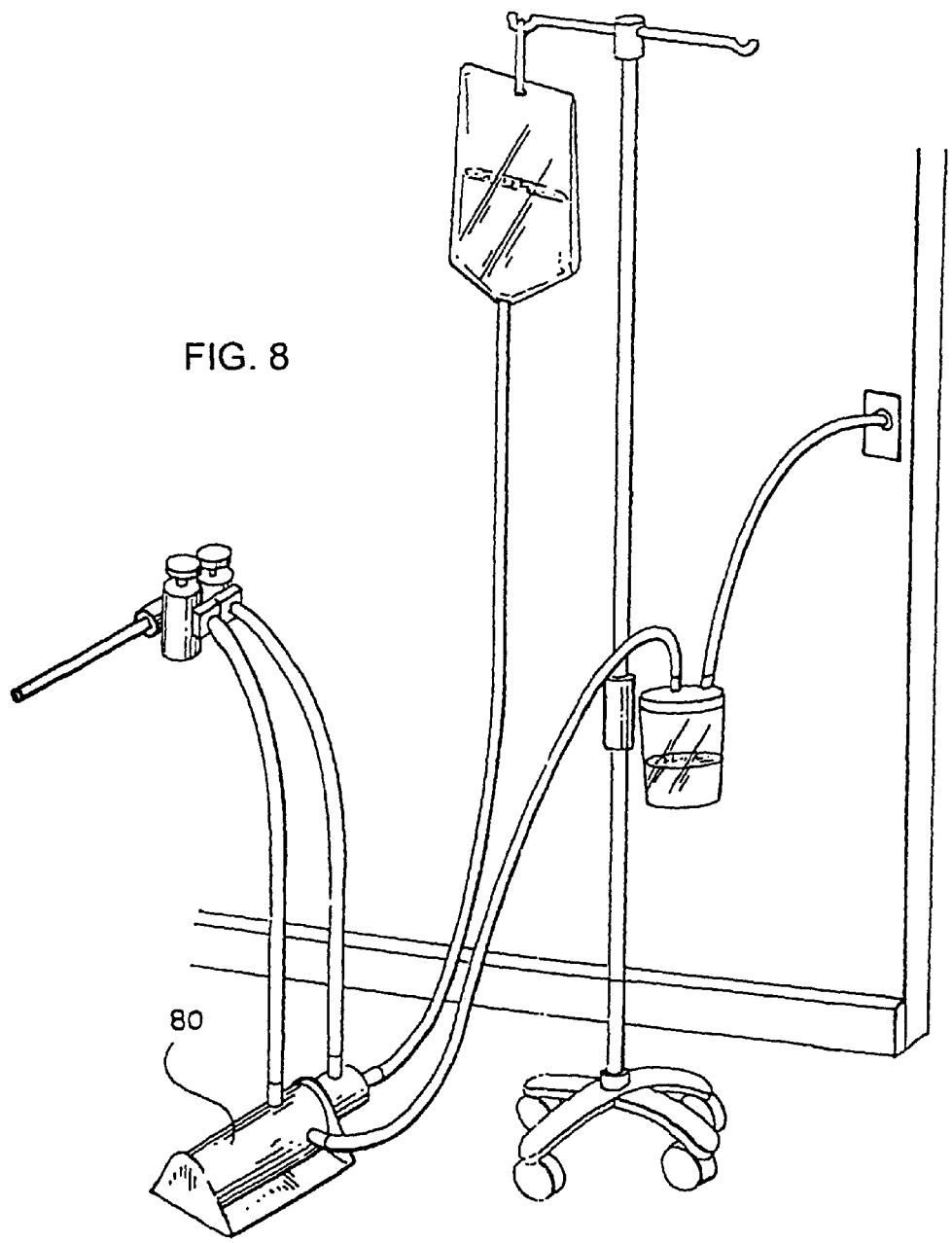
FIG. 8 is a perspective view of an embodiment of the present invention capable of being freestanding without other support structures.
Figure 9:
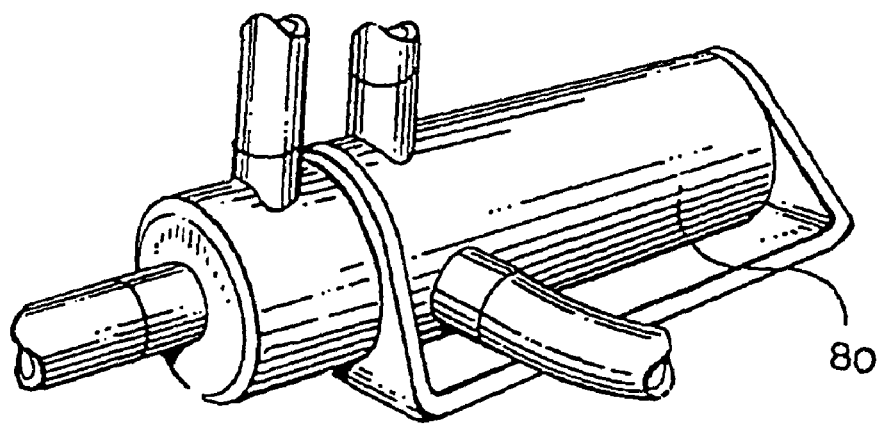
FIG. 9 is an enlarged, perspective view of the pump shown in FIG. 8.
Figure 10:
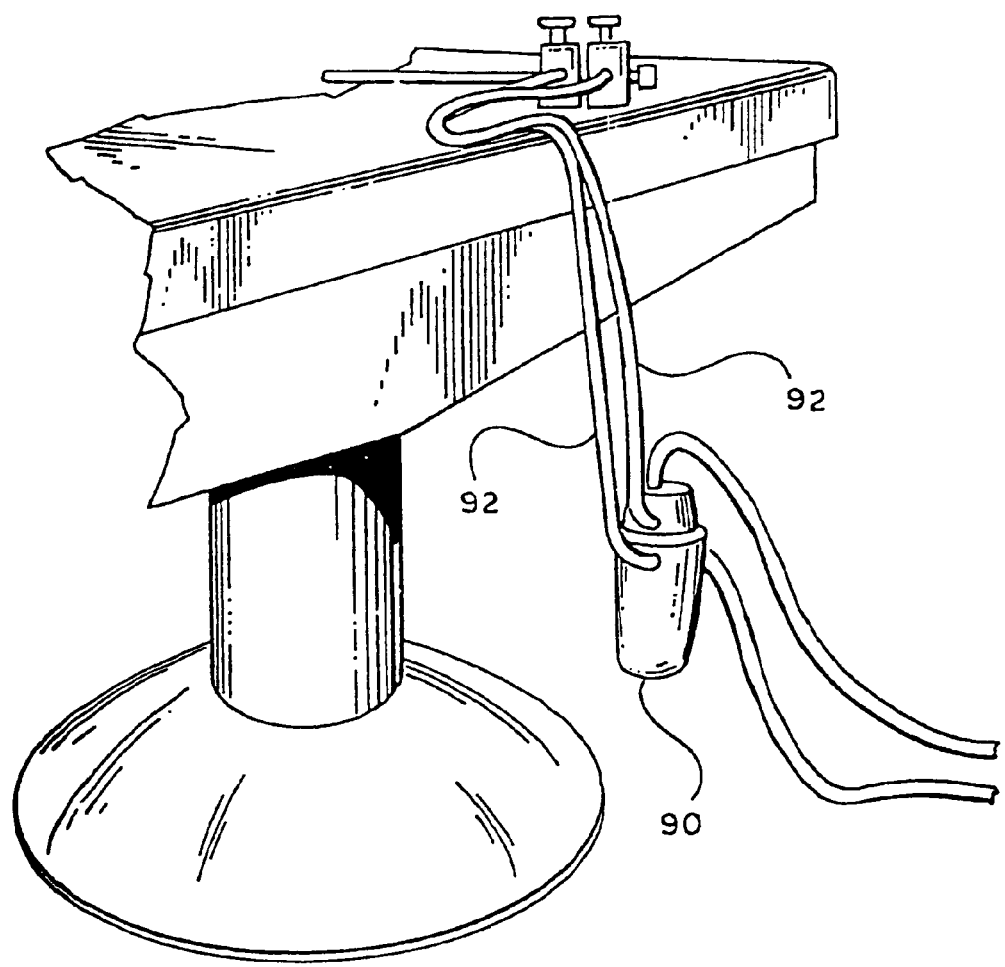
FIG. 10 is a fragmentary, perspective view of an embodiment of the present invention that is incorporated in-line with tubing.

FIG. 8 shows a freestanding pump 80 having no other support structures, FIG. 9 is an enlarged view of the pump of FIG. 8, while FIG. 10 shows an in-line pump 90 that simply hangs on tubing 92.

FIG. 11 shows an exploded view of a stand-alone pump according to the preferred embodiment of the present invention. The pump 200 includes a body or barrel 202, a liquid inlet 208, a vacuum line inlet 210 and O-rings 212 for sealing end caps 214. The pump body or barrel 202 may be transparent to permit monitoring of a pumping operation. Blades 216 and a hub 218 of a rotor, which may be used for a vacuum motor and for a liquid pump, may be of the same or different sizes. One can see that the moving vanes or blades 216 and hub 218 toward the right in the figure are to be disposed in an air motor chamber 226. Similarly, the moving vanes or blades 216 and hub 218 toward the left in the figure are to be disposed in a liquid pump chamber 224. The pump may also be of another construction, such as a centrifugal pump. The pump 200 also includes a dividing web wall 222 inside the pump body or barrel 202 that unevenly divides the air motor chamber 226 from the liquid pump chamber 224. The web wall 222 has an opening 223 formed therein which accepts a seal 225 on a drive shaft 221 supporting both hubs 218, for the motor and the pump. The opening 223 is formed off-center in the web wall 222 so that the axis of the rotors, that is the combined hubs and blades, is radially offset from the central longitudinal axis of the chambers 224, 226 (see FIG. 15).

It is thus seen, that both the rotor in the liquid pump chamber and the rotor in the air motor chamber are eccentric in the respective chambers or offset radially from the central axis of the body or barrel.

Figure 12:
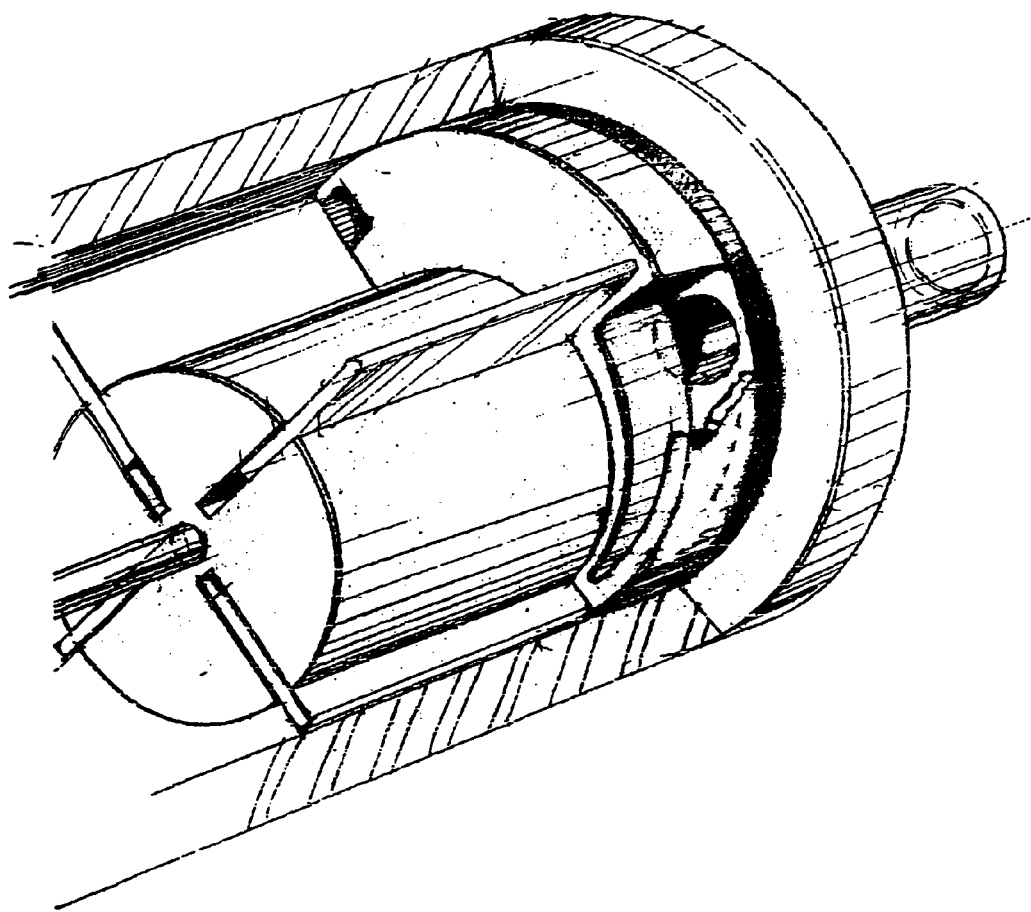
FIG. 12 is a fragmentary, partly broken-away and partly sectional, perspective view of a portion of the pump.

The blades 216 are resiliently connected to the hub 218 by springs 227 partially inserted in blind bores 229 in the blades and fitting over nipples of posts 228 inserted in blind bores 229' in the hub 218. It may also be seen that kidney-shaped pockets 230, 231 are recessed in the end caps 214. The perspective view of FIG. 12 is partly broken-away to show the blades, hub, pockets and ports to be described in greater detail below.

Figure 13A:
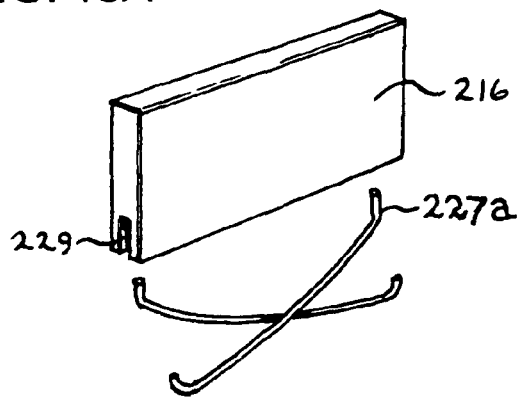
FIGS. 13A, 13B and 13C are perspective views of various valve spring structures.
Figure 13B:
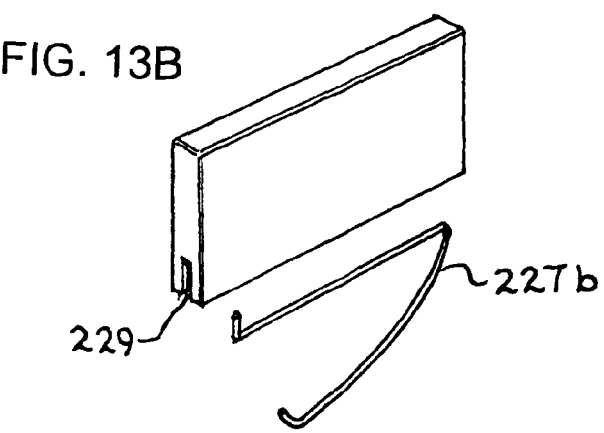
Figure 13C:
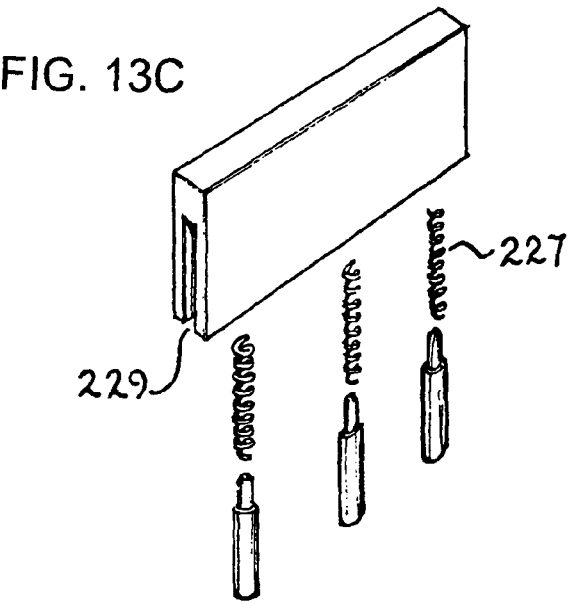

FIGS. 13A, 13B and 13C show various configurations of respective springs 227, 227a and 227b. FIG. 13A shows two leaf springs 227a in an X-shaped configuration, wherein one end of each of the springs is to be inserted into a respective blind bore 229 in a blade 216 while the other end is to be inserted into a respective blind bore 229' in the hub 218. The blind bores 229, 229' may each be in the form of one continuous slot in the blade and the hub, respectively. The leaf spring 227b of FIG. 13B has an approximately V-shape so that one end is to be inserted into a respective blind bore 229 in a blade 216 or one leg of the V-shape may be inserted into a continuous slot in the blade as described above. Similarly, the other end or leg of the V-shape may be inserted into a respective bore or slot in the hub. The illustration of FIG. 13C is an enlarged view of a portion of FIG. 11 showing the spring 227 and bores or slot.

FIG. 14A illustrates an alternative configuration of blade assemblies 316, 317 and a hub 318. It can be seen that the blade assemblies 316, 317 each include two blades and are inserted into respective slots 319, 320. The blade assemblies 316, 317 each have a respective cross-piece 314, 315 disposed at different locations along the blades. The blade assembly 317 is inserted before the blade assembly 316, so that the cross-piece 315 can be disposed further inwardly and the cross-piece 314 can be disposed further outwardly.

FIG. 14B is a cross-sectional view showing a blade 216 in a bore 229'. A spring 227 has one end on a post 228 in the bore 229' and another end in a bore 229 in the blade 216.

An end adapter 321 shown in FIG. 14D is inserted and secured into an open end of the hub 318 after the blade assemblies 316 and 317 are inserted into their respective slots, providing a shaft post.

FIG. 14C is a side-elevational view of one of the hubs 218 having three bores 229' shown in phantom. FIG. 14B is taken along a line XIVB-XIVB of FIG. 14C, in the direction of the arrows.

Figure 15A:
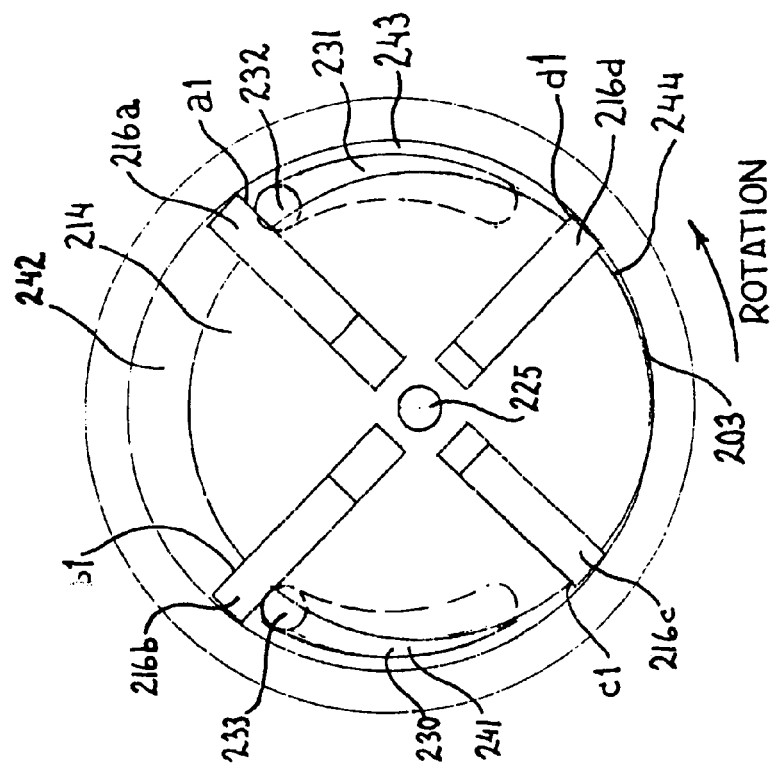
FIGS. 15A, 15B and 15C are cross-sectional views of a portion of a valve blade and barrel assembly in different phases of rotation.
Figure 15B:
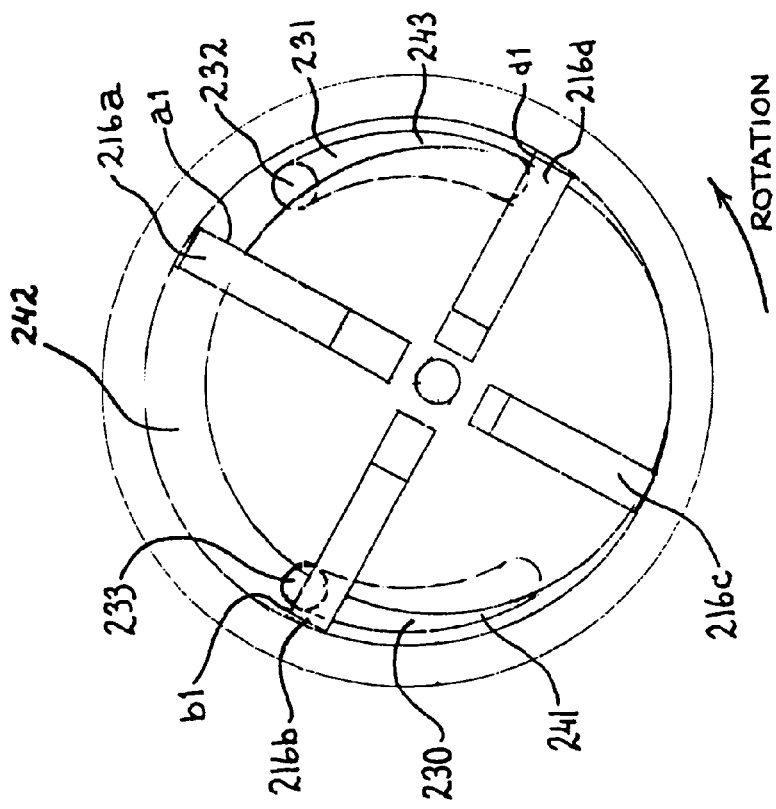
Figure 15C:
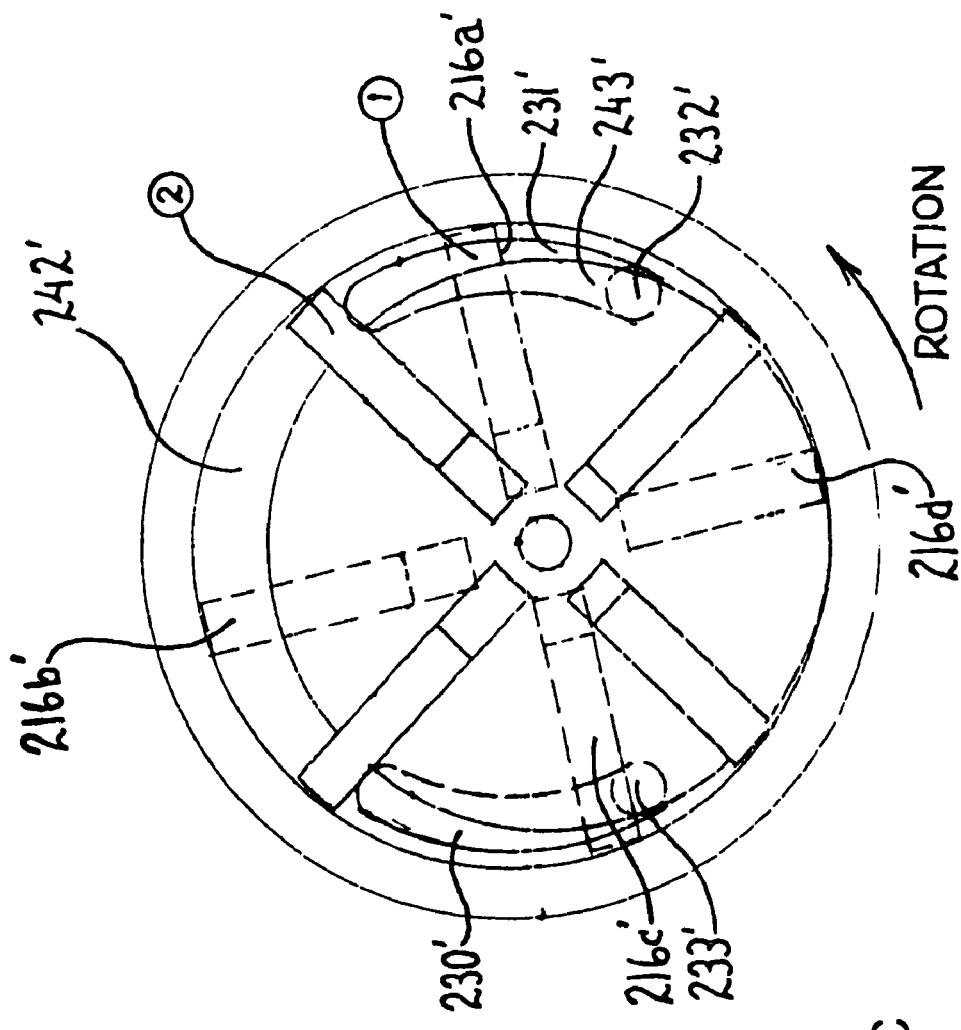

FIGS. 15A, 15B and 15C are cross-sectional views illustrating the operation of the blades 216 in the body or barrel 202 of the pump 200 of FIG. 11. The body or barrel 202 has an inner wall surface 203. The ends of the blades are biased against the inner wall surface 203 by the springs 227. The hub 218 is only diagrammatically illustrated by transverse lines within the blades for simplicity, but the seal 225 is shown. The blades have been given reference numerals 216a, 216b, 216c and 216d for use in the following explanation. The kidney-shaped pockets 230, 231 in one of the end caps 214 are shown as well. Finally, ports 232, 233 are shown leading through the end cap 214.

The following is a description of the operation of the pneumatically driven fluid pump. The device includes a pneumatic vane-type motor directly coupled to a vane-type pump used for pumping fluids.

The operation of the device as a motor will initially be described with reference to FIGS. 15A and 15B. As mentioned above, the springs 227 bias the blades 216a-216d in contact with inner wall surface 203 of the body or barrel 202. The blades 216a-216d define rotor blade cavities 241-244 therebetween within the body or barrel 202. The pockets 230, 231 connect the ports 233, 232 to the cavities 241-244. It is assumed that the blades 216a-216d in FIG. 15A are affected by a vacuum supplied to the port 233 and the port 232 is opened to the atmosphere. The vacuum fills the pocket 230 and the rotor blade cavity 241, causing a force to be exerted on a blade face b1 of the blade 216b. Since the resulting forces are directly related to the area of the blades exposed to the cavity on which the vacuum acts, the resulting force causes a turning moment or torque on the rotor in a counter clock-wise direction moving it to a position shown in FIG. 15B. In FIG. 15A, the blade 216a and the blade 216b have isolated the ports preventing air from passing from the port 232 to the port 233.

In FIG. 15B, the position of the blade 216a blocks communication between the port 232 and the port 233, and the position of the blade 216b opens access to the port 233 allowing air to escape. As the rotor turns in FIG. 15B, a blade face a1 of the blade 216a has a greater area than a blade face d1 of the blade 216d, generating a larger force on the blade 216a than on the blade 216d, again turning the rotor in a counter-clockwise direction. The porting is symmetrical and applying a vacuum to the port 232 will rotate the motor in a clockwise direction.

The operation of the device as a pump will now be described. A vane motor can also be operated as a vane pump. FIG. 15C shows the pump blades in two positions, indicated as position 1 in broken lines and position 2 in solid lines. In the position 1 in FIG. 15C, the fluid applied to the port 232' fills the kidney shaped pocket 231' in the end cap and also flows into the rotor blade cavity 242' between the blades 216a' and 216b' and into the cavity 243' between the blades 216a' and 216d'.

The blades are rotated counterclockwise into the position 2 in FIG. 15C. The pockets 231' and 230' are now isolated from each other and fluid is trapped in the cavity 242'. Further rotation of the blade 216b' uncovers the upper end of the pocket 230', which contains the exit port 233'. As the rotor and the blades continue to turn, the volume in the cavity 242' decreases, forcing the fluid out of the port 233'. During rotation, the volume of the cavity between the blades 216a' and 216d' is increasing, drawing fluid from the port 232' into the pocket 231' and into the cavity 243' between the blades 216a' and 216d'.

Figure 16:
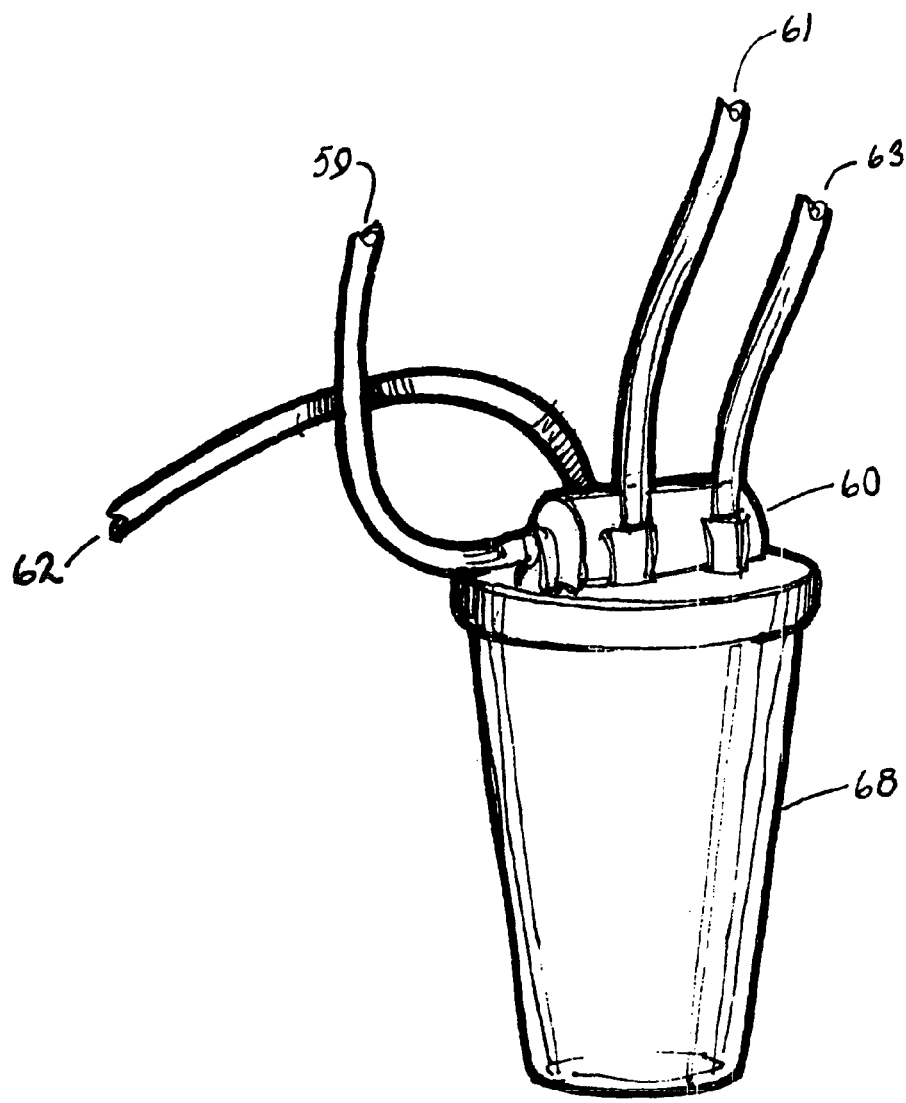
FIG. 16 is a perspective view showing the pump as an integral part of a top cover of a suction canister.

FIG. 16 shows an embodiment in which the pump 60 is an integral part of a cover of a suction canister 68. This figure shows the suction source 63, the tubing carrying the fluid to the trumpet valve from the pump 61, the line to the IV bag source of fluid 59 and the suction line to the trumpet valve 62.

Figure 27:
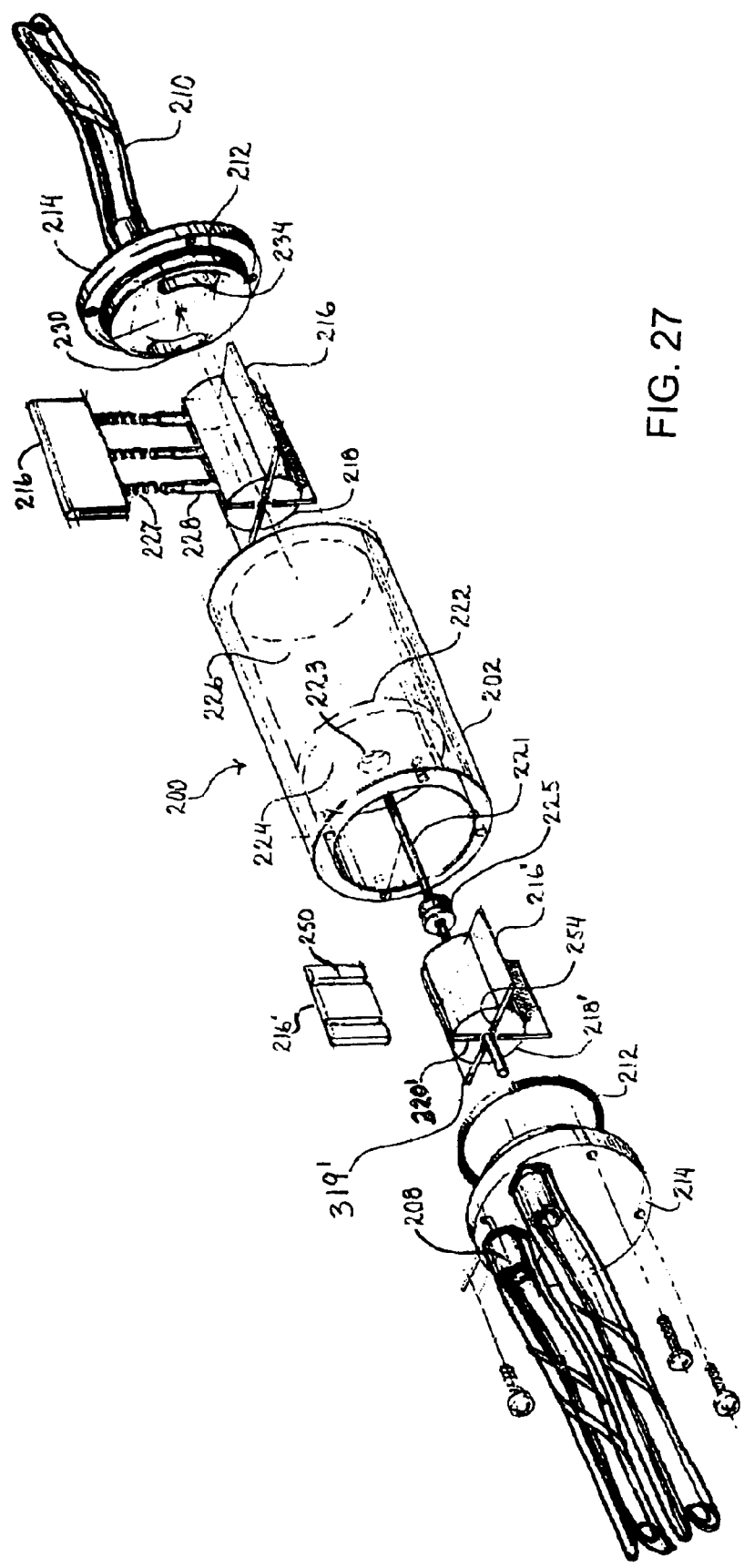
FIG. 27 is an exploded, perspective view, similar to FIG. 11, of a stand-alone pump according to another embodiment of the present invention in which the blades of the liquid pump rotor are not spring-mounted and have pressure relief channels.
Figure 28:
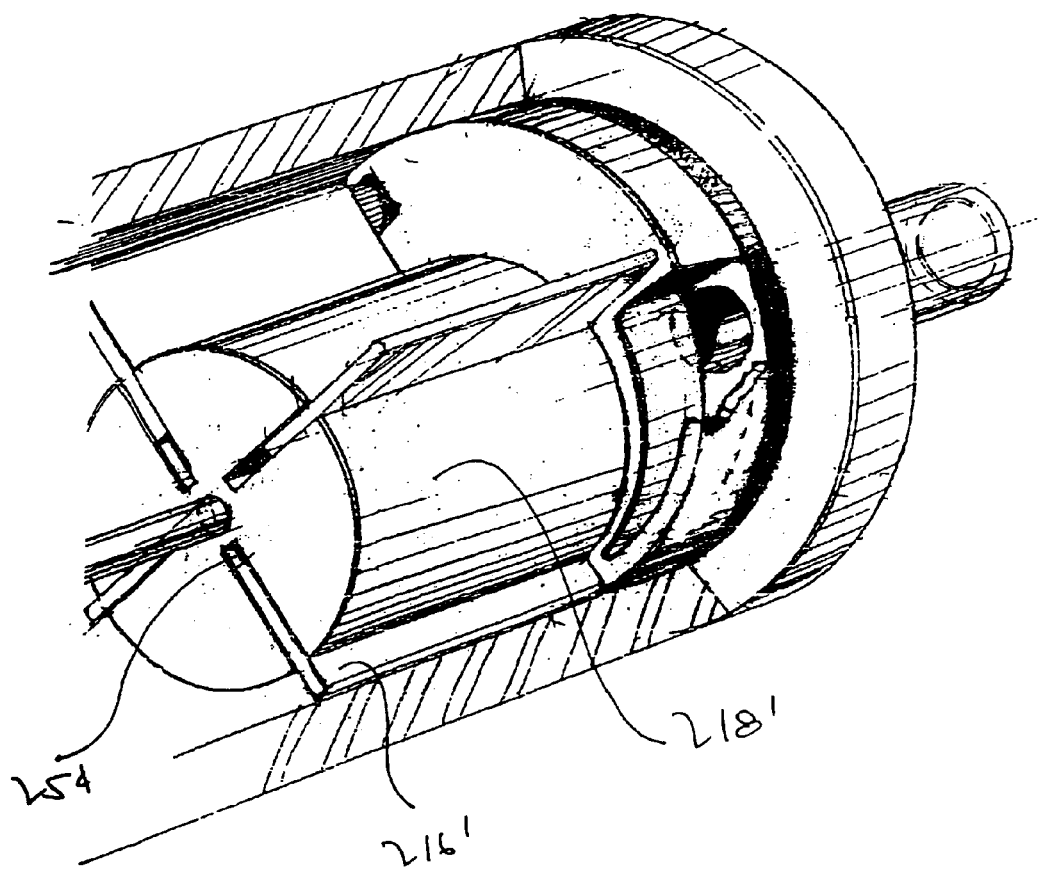
FIG. 28 is a fragmentary, partly broken-away and partly sectional, perspective view, similar to FIG. 12, of a portion of the pump showing trapped liquid to be removed according to the invention.
Figure 29:
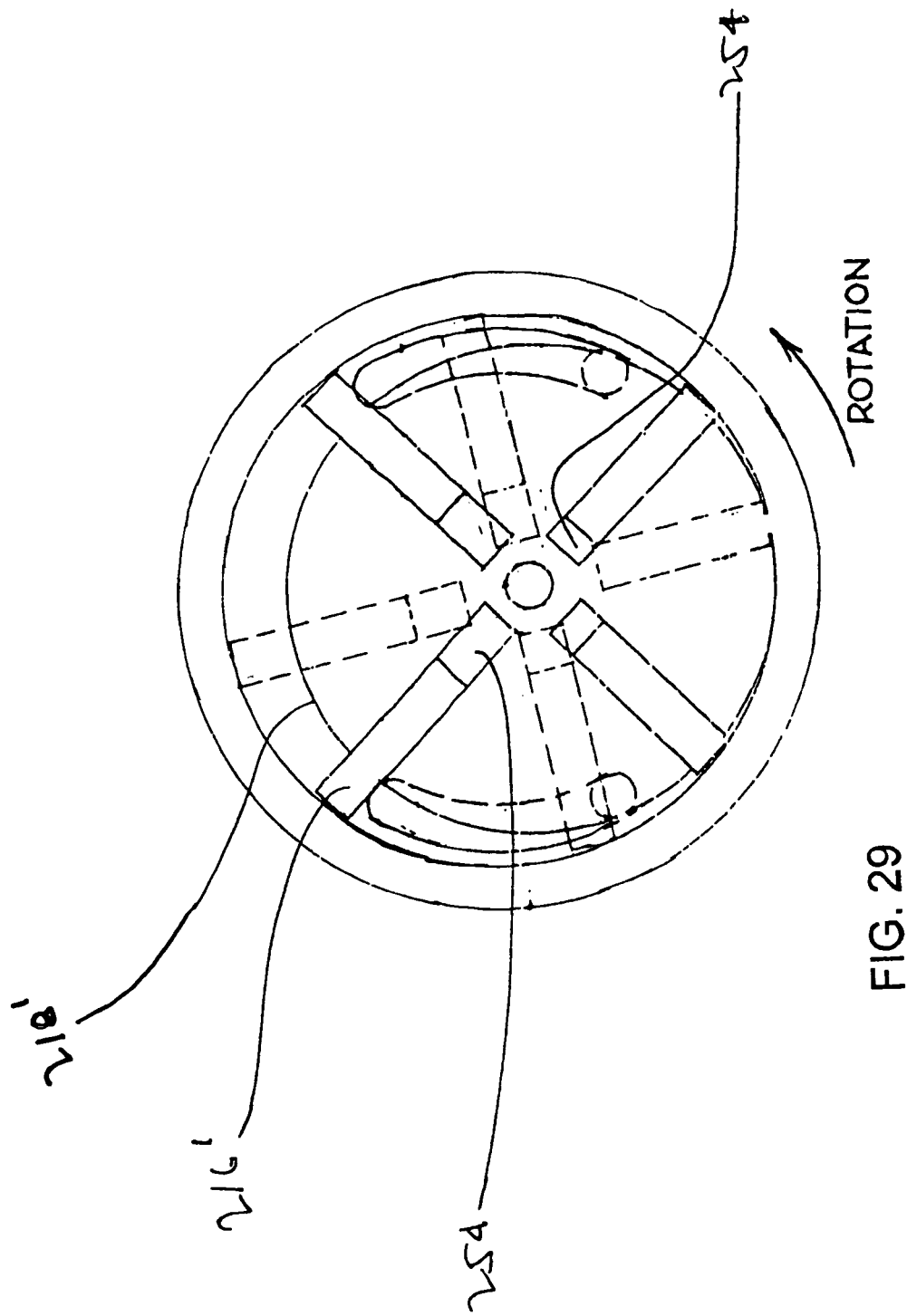
FIG. 29 is a cross-sectional view of a portion of a rotor blade and barrel assembly in different phases of rotation, also showing trapped liquid to be removed according to the invention.
Figure 30A:
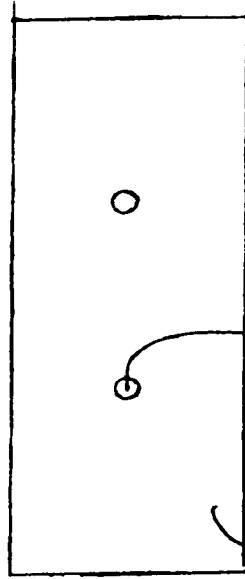
FIGS. 30A, 30B, 30C and 30D are respective front-elevational, side-elevational, top-plan and perspective views of liquid pump rotor blades having relief holes passing through lateral surfaces of the blade.
Figure 30B:
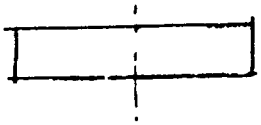
Figure 30C:
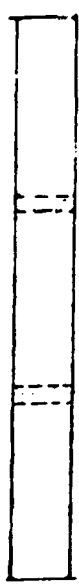
Figure 30D:
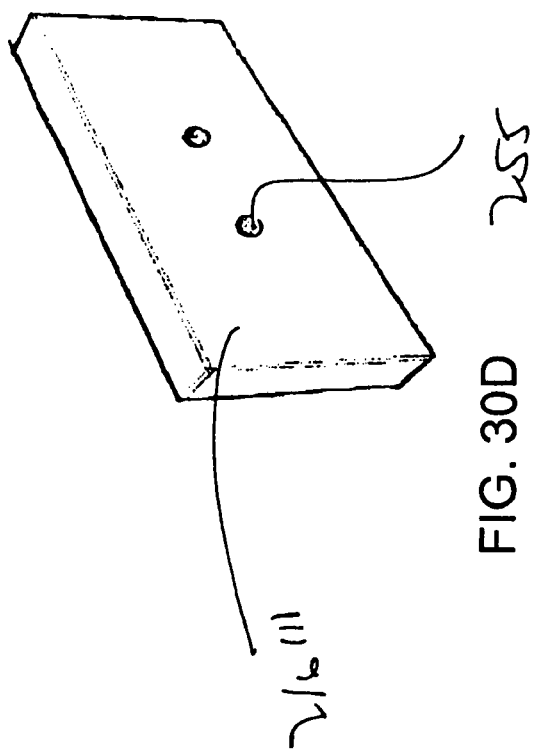

FIGS. 17A, 17B and 17C illustrate a first embodiment of a pressure relieving rotor blade 216'. The rotor blade 216' is part of a device for pumping fluid according to the invention, which is shown in FIG. 27. According to the embodiment of FIGS. 17A, 17B and 17C, two pressure relief channels 250 are formed in one lateral surface of the rotor blade 216'. The channels are directed radially along the lateral surface from the bottom of slots 319', 320' in a hub 218' receiving the blade toward a body or barrel 202, as shown in FIG. 27. The channels 250 guide fluid or fluid, especially water, to relieve pressure under each rotor blade. Trapped water 254 to be relieved from under the blade along the channels 250 is indicated in FIGS. 27, 28 and 29. The relief of the trapped water leads to reduced pump requirements and significantly increases output of the device for pumping fluid.

It is understood that any number of channels 250 may be provided in either or both lateral surfaces of the blade. Some variation in direction is also possible, as long as the channels serve to guide the fluid or fluid radially outwardly.

FIGS. 18A, 18B and 18C illustrate a second embodiment of a pressure relieving rotor blade 216". In this embodiment, a pressure relief hole 251 is formed radially through the blade 216" from the hub toward the body or barrel for relieving the trapped water 254. The hole may be a smaller diameter, extension of a blind bore, if the blade has a blind bore for receiving a spring, as seen in FIGS. 11 and 27. Once again, more than one hole 251 may be provided and there may be some variation in direction, as long as the fluid or fluid is generally radially outwardly directed.

FIGS. 30A, 30B, 30C and 30D illustrate a third embodiment of a pressure relieving rotor blade 216'''. In this embodiment, pressure relief holes 255 are formed through the blade from one lateral surface to the other in circumferential direction of the body or barrel 202. The size, number, placement and direction of the holes maybe varied, to balance the pressure on the two radial surfaces of the blade, allowing the blades to rotate faster and therefore push more fluid or fluid in the liquid pump chamber 224.

FIGS. 19A, 19B, 19C and 19D show a fourth embodiment for pressure relief according to the invention. In this embodiment, pressure relief holes 252 are formed in the bottom of the slots 319', 320' receiving the blades, which are seen in FIG. 27. The holes 252 lead from the slots 319', 320' toward the center of the hub 218', so as to direct the trapped fluid or fluid 254 into a drive shaft hole in the hub around the drive shaft 221. This embodiment is not limited to the two radially directed holes as shown, as long as the trapped water is guided radially inwardly to relieve pressure.

FIGS. 20A, 20B, 20C and 20D also provide pressure relief within the hub 218'. However, according to this fifth pressure relief embodiment, pressure relief channels 253 are formed in lateral surfaces of the slots 319', 320' receiving the blades, which are seen in FIG. 27. Any number of channels 253 may be provided in either or both lateral surfaces of the slots and need not be exactly radially directed, as long as they serve to direct the trapped water outwardly to relieve pressure.

Each of the channels 250 and 253 and the holes 251, 252 and 255 represent at least one conduit relieving pressure on the assembly of the rotating hub and blades by conducting fluid.

FIGS. 21A-21B, 22A-22B, 23A-23B, 24A-24B, 25A-25B and 26A-26B show various edge shapes of rotor blades according to the invention. Each of FIGS. 21A, 22A, 23A, 24A, 25A and 26A show an air motor hub 218 according to FIG. 27, although it is understood that these embodiments of the invention could also be applied to the liquid pump hub 218'.

Each of FIGS. 21B, 22B, 238, 24B, 25B and 26B show a respective blade 216.1. 216.2, 216.3, 216.4, 216.5 and 216.6 which is to be inserted into a slot in the hub. The outer edges of the blades which approach the inner surface of the body or barrel 202 shown in FIG. 27 have different shapes for minimizing friction between the blade as it rotates and the inner cylindrical surface of the body or barrel. This reduction in friction is due to a force vector parallel to the blade, in a direction toward the center shaft 221, which is generated due to the shape of the radially outer edge of the blade, when an inlet air force or fluid or fluid force is present in a direction perpendicular to the blade.

Figure 22A:
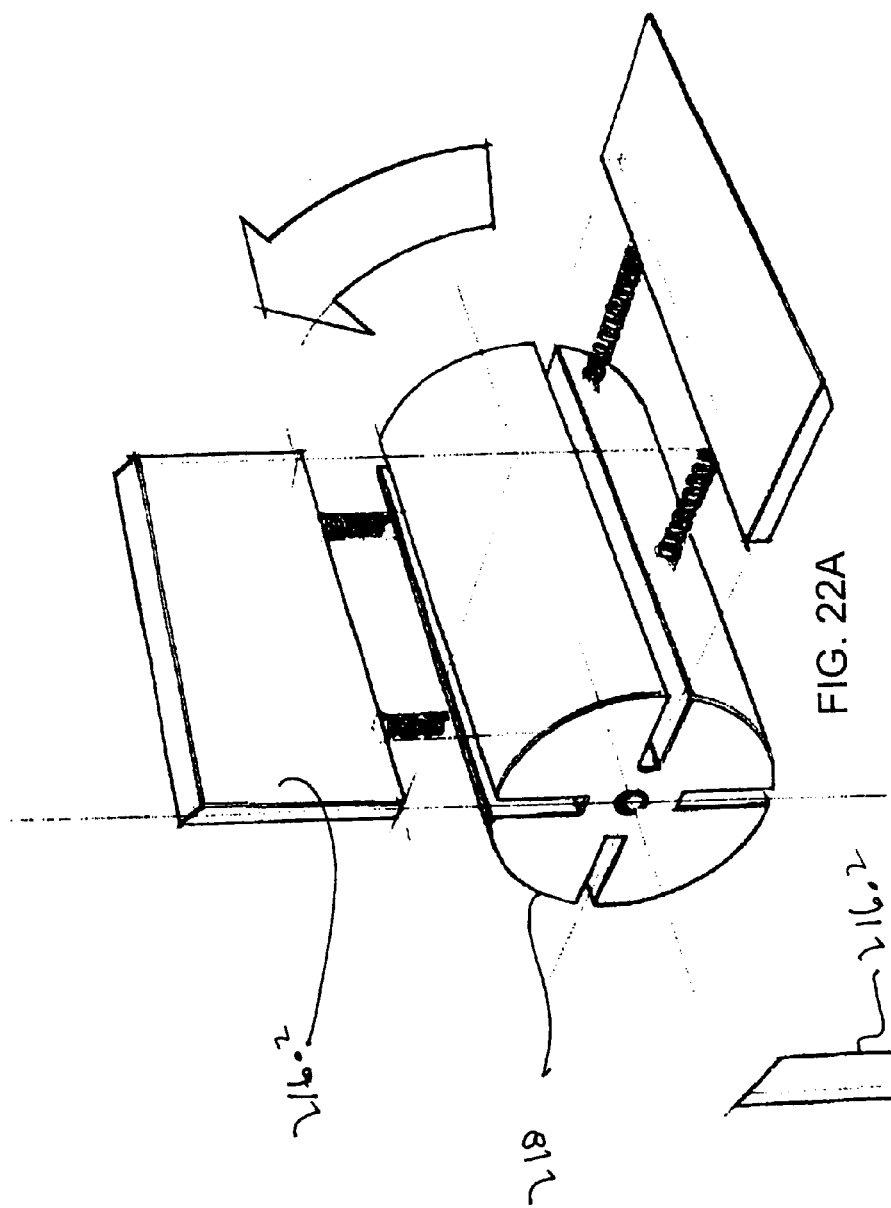
FIGS. 22A and 22B are respective exploded perspective and side-elevational views of a rotor and blades having an edge beveled against the direction of rotation of the blade.
Figure 22B:
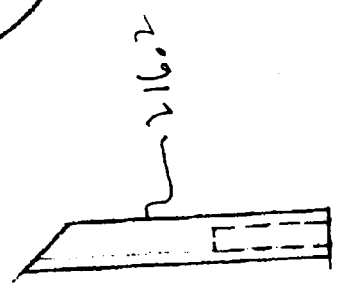
Figures 23A, 23B:
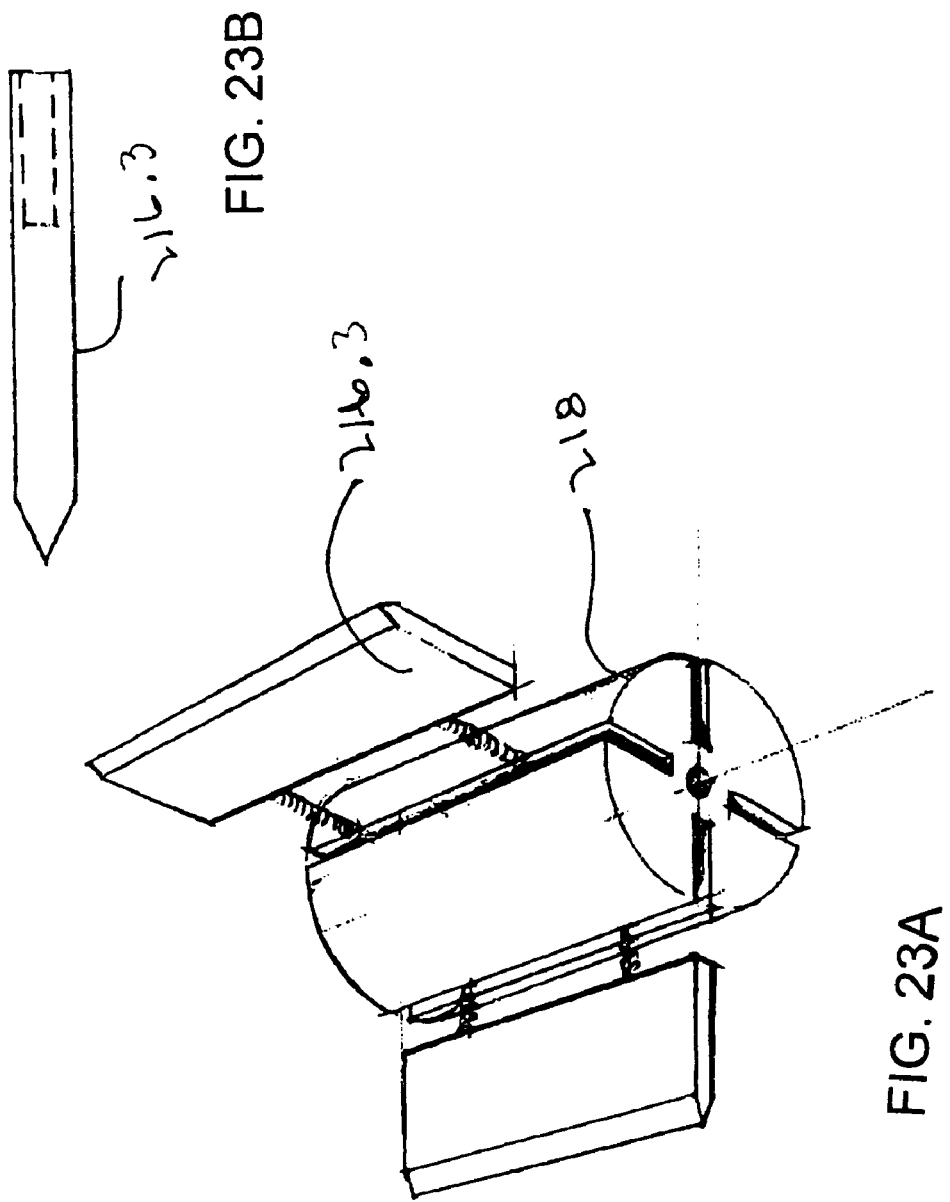
FIGS. 23A and 23B are respective exploded perspective and side-elevational views of a rotor and blades having a double edge beveled both along and against the direction of rotation of the blade.

More specifically, the radially outer edge of the blade 216.1 in FIG. 21B has a shape which is beveled along the direction of rotation of the blade, whereas the radially outer edge of the blade 216.2 in FIG. 22B has a shape which is beveled against the direction of rotation of the blade. In each case, the direction of rotation of the blades is indicated by an arrow. The radially outer edge of the blade 216.3 in FIG. 23B has a double edge shape which is beveled both along and against the direction of rotation of the blade. The radially outer edge of the blade 216.4 in FIG. 24B has a convexly rounded shape.

Figure 25A:
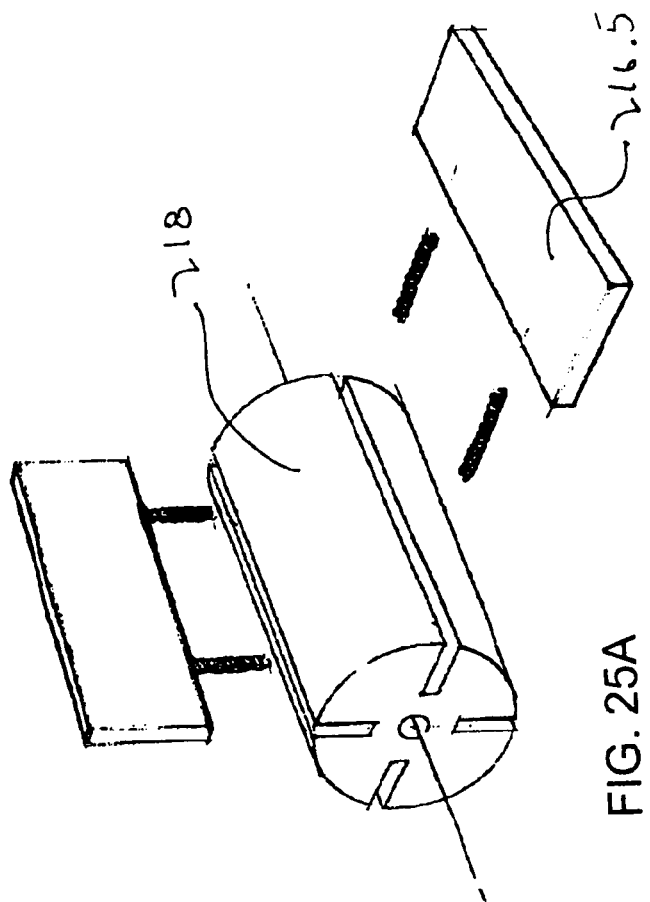
FIGS. 25A and 25B are respective exploded perspective and side-elevational views of a rotor and blades having an edge perpendicular to the sides of the blade.
Figure 25B:
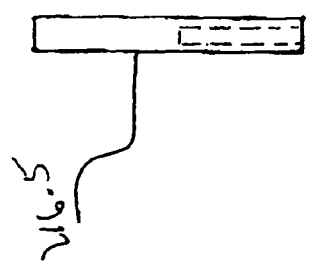

The radially outer edge of the blade 216.5 in FIG. 25B has a shape with a surface perpendicular to the lateral surfaces of the blade. Finally, the radially outer edge of the blade 216.6 in FIG. 26B has a concave shape.

As mentioned above, FIG. 27 is a view similar to FIG. 11, showing the entire device for pumping fluid according to the invention. However, in contrast to FIG. 11, the device shown in FIG. 27 does not have springs mounting the blades in the hub of the rotor in the liquid pump shown on the left side of the figure. Instead, a blade 216' having the channels 250 is shown. Of course, the blades of FIG. 18 or 30, the slots of FIGS. 19 and 20 or the blades of FIGS. 21-26 may instead be provided in the device shown in FIG. 27.

FIG. 28 is similar to FIG. 12, except that it indicates the trapped water 254, as discussed above.

FIG. 29 illustrates the operation of the assembly having the hub 218' and blades 216'. The operation of the assembly is described with regard to FIGS. 15a and 15b, whereas FIG. 29 shows the trapped fluid or fluid 254.

It should be understood, of course, that the foregoing relates only to preferred embodiments of the present invention and that numerous modifications or alterations may be made therein without departing from the spirit and the scope of the invention as set forth in the appended claims. For example, the pressure relief channels or holes in the blades may be combined with the pressure relief channels or holes in the slots and/or the edge shapes of the blades.

We claim:

1. A pump, comprising:
   a pumping chamber having an inlet;
   an assembly disposed in said pumping chamber, said assembly having a rotating hub, blades mounted on said rotating hub, and at least one conduit relieving pressure on said assembly by conducting fluid;
   a connection to a fluid source; and
   a connection to an air source.

2. The pump according to claim 1, wherein said blades each have outer surfaces, and said at least one conduit is at least one radially directed channel formed in at least one of said outer surfaces for relieving said pressure on said assembly by conducting trapped fluid radially outwardly.

3. The pump according to claim 1, wherein said at least one conduit is at least one radially directed hole formed in each of said blades for relieving said pressure on said assembly by conducting trapped fluid radially outwardly.

4. The pump according to claim 1, wherein said blades each have lateral surfaces, and said at least one conduit is at least one hole passing through said blade from one of said lateral surfaces to another of said lateral surfaces for relieving said pressure on said assembly by conducting fluid through said at least one hole.

5. The pump according to claim 1, wherein said hub has slots formed therein for receiving said blades, said slots having slot bottoms, and said at least one conduit is at least one radially directed hole formed in each of said slot bottoms for relieving said pressure on said assembly by conducting trapped fluid from said slot bottoms.

6. The pump according to claim 5, which further comprises a drive shaft, said rotating hub having a hole formed therein for receiving said drive shaft and for receiving the trapped fluid conducted from said at least one radially directed hole.

7. The pump according to claim 1, wherein said hub has slots formed therein for receiving said blades, said slots having lateral surfaces, and said at least one conduit is at least one radially directed channel formed in at least one of said lateral surfaces for relieving said pressure on said assembly by conducting trapped fluid radially outwardly.

8. The pump according to claim 1, further comprising:
an air motor chamber having an inlet; and
another assembly disposed in said air motor chamber, said other assembly having a rotating hub and blades mounted on said rotating hub;
said assemblies rotating together.

9. The pump according to claim 8, further comprising:
end caps each disposed at a respective one of said chambers;
said end cap of said air motor chamber having ports and blind pockets formed therein for conducting air to create different pressures at surfaces of said blades in said air motor chamber for rotating said blades.

10. The pump according to claim 8, further comprising:
end caps each disposed at a respective one of said chambers;
said end cap of said pumping chamber having ports and blind pockets formed therein for conducting fluid due to different pressures at surfaces of said blades in said pumping chamber caused by rotating said blades.

11. The pump according to claim 8, wherein said rotating hubs of said assemblies have an axis being radially offset from a central longitudinal axis of said chambers.

12. The pump according to claim 1, wherein the pump pumps the fluid for a procedure selected from the group consisting of laparoscopy, open surgery, orthopedics, oral surgery, arthroscopy, endoscopy, wound cleansing, liposuction and gynecology.

13. A pump, comprising:
a pumping chamber having an inner surface and an inlet;
an assembly disposed in said pumping chamber, said assembly having a rotating hub and blades mounted on said rotating hub, said blades each having a radially outer edge with a shape minimizing friction between said radially outer edge and said inner surface of said pumping chamber;
a connection to a fluid source; and
a connection to an air source.

14. The pump according to claim 13, wherein said hub rotates in a direction of rotation, and said radially outer edge is beveled along said direction of rotation.

15. The pump according to claim 13, wherein said hub rotates in a direction of rotation, and said radially outer edge is beveled against said direction of rotation.

16. The pump according to claim 13, wherein said radially outer edge has two intersecting bevels.

17. The pump according to claim 13, wherein said radially outer edge is rounded.

18. The pump according to claim 13, wherein said blades each have lateral surfaces, and said radially outer edge has a surface perpendicular to said lateral surfaces.

19. The pump according to claim 13, wherein said radially outer edge is concave.

20. The pump according to claim 13, further comprising:
an air motor chamber having an inlet; and
another assembly disposed in said air motor chamber, said other assembly having a rotating hub and blades mounted on said rotating hub;
said assemblies rotating together.

21. The pump according to claim 20, further comprising:
end caps each disposed at a respective one of said chambers;
said end cap of said air motor chamber having ports and blind pockets formed therein for conducting air to create different pressures at surfaces of said blades in said air motor chamber for rotating said blades.

22. The pump according to claim 20, further comprising:
end caps each disposed at a respective one of said chambers;
said end cap of said pumping chamber having ports and blind pockets formed therein for conducting fluid due to different pressures at surfaces of said blades in said pumping chamber caused by rotating said blades.

23. The pump according to claim 20, wherein said rotating hubs of said assemblies have an axis being radially offset from a central longitudinal axis of said chambers.

24. The pump according to claim 13, wherein the pump pumps the fluid for a procedure selected from the group consisting of laparoscopy, open surgery, orthopedics, oral surgery, arthroscopy, endoscopy, wound cleansing, liposuction and gynecology.

25. A method for providing fluid, which comprises the following steps:
a) providing a pump connected to a source for fluid and a source for air, the pump having an assembly with a rotating hub and blades mounted on the rotating hub;
b) driving the pump with a vacuum;
c) pumping the fluid to a site; and
d) relieving pressure on the assembly by conducting fluid through at least one conduit.

26. The method according to claim 25, which further comprises carrying out the step of relieving pressure on the assembly by conducting trapped fluid radially outwardly through at least one respective radially directed channel formed in at least one outer surface of each of the blades.

27. The method according to claim 25, which further comprises carrying out the step of relieving pressure on the assembly by conducting trapped fluid radially outwardly through at least one respective radially directed hole formed in each of the blades.

28. The method according to claim 25, which further comprises carrying out the step of relieving pressure on the assembly by conducting fluid through at least one hole passing through each respective one of the blades from one lateral surface to another lateral surface of the blades.

29. The method according to claim 25, which further comprises providing blade-receiving slots with slot bottoms in the hub, and carrying out the step of relieving pressure on the assembly by conducting trapped fluid through at least one respective radially directed hole formed in each slot bottom.

30. The method according to claim 29, which further comprises providing a drive shaft supporting the rotating hub and passing through a drive shaft hole in the rotating hub, and conducting the trapped fluid from the at least one respective radially directed hole into the drive shaft hole in the rotating hub.

31. The method according to claim 25, which further comprises providing blade-receiving slots with lateral surfaces in the hub, and carrying out the step of relieving pressure on the assembly by conducting trapped fluid through at least one radially directed channel formed in at least one of the lateral surfaces.

32. The method according to claim 25, which further comprises:
providing an air motor chamber having an inlet;
providing another assembly in the air motor chamber, the other assembly having a rotating hub and blades mounted on the rotating hub; and
rotating the assemblies together.

33. The method according to claim 32, which further comprises:
providing end caps each at a respective one of the chambers; and conducting air through ports and blind pockets formed in the end cap of the air motor chamber to create different pressures at surfaces of the blades in the air motor chamber for rotating the blades.

34. The method according to claim 32, which further comprises:
providing end caps each at a respective one of the chambers; and
conducting fluid through ports and blind pockets formed in the end cap of the pumping chamber due to different pressures at surfaces of the blades in the pumping chamber caused by rotating the blades.

35. The pump according to claim 32, which further comprises radially offsetting an axis of the rotating hubs of the assemblies from a central longitudinal axis of the chambers.

36. The method according to claim 25, further comprising carrying out the method in a procedure selected from the group consisting of laparoscopy, open surgery, orthopedics, oral surgery, arthroscopy, endoscopy, wound cleansing, liposuction and gynecology.

37. A method for providing fluid, which comprises the following steps:
a) providing a pump connected to a source for fluid and a source for air, the pump having a pumping chamber and an assembly with a rotating hub and blades mounted on the rotating hub;
b) driving the pump with a vacuum;
c) pumping the fluid to a site; and
d) minimizing friction between radially outer edges of the blades and an inner surface of the pumping chamber.

38. The method according to claim 37, which further comprises rotating the hub in a direction of rotation, and carrying out the step of minimizing friction between radially outer edges of the blades and an inner surface of the pumping chamber by beveling the radially outer edges along the direction of rotation.

39. The method according to claim 37, which further comprises rotating the hub in a direction of rotation, and carrying out the step of minimizing friction between radially outer edges of the blades and an inner surface of the pumping chamber by beveling the radially outer edges against the direction of rotation.

40. The method according to claim 37, which further comprises carrying out the step of minimizing friction between radially outer edges of the blades and an inner surface of the pumping chamber by providing each of the radially outer edges with two intersecting bevels.

41. The method according to claim 37, which further comprises carrying out the step of minimizing friction between radially outer edges of the blades and an inner surface of the pumping chamber by rounding each of the radially outer edges.

42. The method according to claim 37, which further comprises carrying out the step of minimizing friction between radially outer edges of the blades and an inner surface of the pumping chamber by providing the blades with lateral surfaces and providing each of the radially outer edges with a surface perpendicular to the lateral surfaces.

43. The method according to claim 37, which further comprises carrying out the step of minimizing friction between radially outer edges of the blades and an inner surface of the pumping chamber by providing the radially outer edges with a concave shape.

44. The method according to claim 37, which further comprises:
providing an air motor chamber having an inlet;
providing another assembly in the air motor chamber, the other assembly having a rotating hub and blades mounted on the rotating hub; and
rotating the assemblies together.

45. The method according to claim 44, which further comprises:
providing end caps each at a respective one of the chambers; and
conducting air through ports and blind pockets formed in the end cap of the air motor chamber to create different pressures at surfaces of the blades in the air motor chamber for rotating the blades.

46. The method according to claim 44, which further comprises:
providing end caps each at a respective one of the chambers; and
conducting fluid through ports and blind pockets formed in the end cap of the pumping chamber due to different pressures at surfaces of the blades in the pumping chamber caused by rotating the blades.

47. The pump according to claim 44, which further comprises radially offsetting an axis of the rotating hubs of the assemblies from a central longitudinal axis of the chambers.

48. The method according to claim 37, further comprising carrying out the method in a procedure selected from the group consisting of laparoscopy, open surgery, orthopedics, oral surgery, arthroscopy, endoscopy, wound cleansing, liposuction and gynecology.

* * * * *